(12) United States Patent
Noguchi

(10) Patent No.: US 11,026,986 B2
(45) Date of Patent: Jun. 8, 2021

(54) BEETROOT-CONTAINING COMPOSITION

(71) Applicant: Mission Salt, Inc., San Francisco, CA (US)

(72) Inventor: Seiichi Noguchi, Tokyo (JP)

(73) Assignee: Mission Salt, Inc., San Francisco, CA (US)

( * ) Notice: Subject to any disclaimer, the term of this patent is extended or adjusted under 35 U.S.C. 154(b) by 0 days.

(21) Appl. No.: 16/130,928

(22) PCT Filed: Mar. 9, 2018

(86) PCT No.: PCT/JP2018/010668
§ 371 (c)(1),
(2) Date: Sep. 13, 2018

(87) PCT Pub. No.: WO2018/173985
PCT Pub. Date: Sep. 27, 2018

(65) Prior Publication Data
US 2020/0078428 A1   Mar. 12, 2020

(30) Foreign Application Priority Data

Mar. 23, 2017 (JP) .............................. JP2017-057287
Jun. 22, 2017 (JP) .............................. JP2017-122074

(51) Int. Cl.
*A61K 36/21* (2006.01)
*A61P 9/12* (2006.01)
*A61K 9/00* (2006.01)
*A61K 36/48* (2006.01)

(52) U.S. Cl.
CPC ............ *A61K 36/21* (2013.01); *A61K 9/0056* (2013.01); *A61K 36/48* (2013.01); *A61P 9/12* (2018.01)

(58) Field of Classification Search
None
See application file for complete search history.

(56) References Cited

U.S. PATENT DOCUMENTS

| | | | |
|---|---|---|---|
| 2008/0260934 A1* | 10/2008 | Bok ....................... | A23L 13/426 426/648 |
| 2010/0047344 A1* | 2/2010 | Lundberg ................. | A23L 2/52 424/466 |
| 2015/0366901 A1 | 12/2015 | Chirinos | |

FOREIGN PATENT DOCUMENTS

| | | |
|---|---|---|
| CN | 102 687 831 A | 9/2012 |
| CN | 102687831 A * | 9/2012 |
| CN | 103 734 826 A | 4/2014 |
| CN | 103734826 A * | 4/2014 |
| WO | 2010/035253 A1 | 4/2010 |

OTHER PUBLICATIONS

Carlström et al., "Dietary nitrate attenuates oxidative stress, prevents cardiac and renal injuries, and reduces blood pressure in salt-induced hypertension," Cardiovascular Research, vol. 89, pp. 574-585 (2011).
Chen et al., "?-Arginine Abrogates Salt-sensitive Hypertension in Dahl/Rapp Rats," J. Clin. Invest., vol. 88, pp. 1559-1567 (Nov. 1991).
Fujiwara et al., "Study on the Relationship Between Plasma Nitrite and Nitrate Level and Salt Sensitivity in Human Hypertension—Modulation of Nitric Oxide Synthesis by Salt Intake," Circulation, vol. 101, pp. 856-861 (2000).
Gee et al., "Dietary Nitrate Lowers Blood Pressure: Epidemiological, Pre-clinical Experimental and Clinical Trial Evidence," Curr. Hypertens. Rep., vol. 18, pp. 16-29 (2016).
International Search Report and Written Opinion, International Application No. PCT/JP2018/010668 (published under WO 2018/173985), 13 pages (dated Jun. 22, 2018).
Jonvik et al., "Nitrate-Rich Vegetables Increase Plasma Nitrate and Nitrite Concentrations and Lower Blood Pressure in Healthy Adults," The Journal of Nutrition, vol. 146, pp. 986-993 (Apr. 13, 2016).
Kapil et al., "Dietary nitrate provides sustained blood pressure lowering in hypertensive patients: a randomized, phase 2, double-blind, placebo-controlled study," Hypertension, vol. 65, No. 2, pp. 320-327 (Feb. 2015).
Morris, Jr., et al., "How Does High Salt Intake Cause Hypertension? Vasodysfunction That Involves Renal Vasodysfunction, Not Abnormally Increased Renal Retention of Sodium, Accounts for the Initiation of Salt-Induced Hypertension," Circulation, vol. 137, pp. 881-893 (2016).
Schatz et al., "Elementary immunology: Na+ as a regulator of immunity," Pediatr. Nephrol., vol. 32, pp. 201-210 (2017.
Sobko et al., "Dietary nitrate in Japanese traditional foods lowers diastolic blood pressure in healthy volunteers," Nitric Oxide, vol. 22, pp. 136-140 (2010).

* cited by examiner

*Primary Examiner* — Ralph J Gitomer
(74) *Attorney, Agent, or Firm* — Holzer Patel Drennan

(57) ABSTRACT

An enhanced food composition in the form of a soup, sauce or condiment is described, the enhanced food composition comprising a nitrate-containing vegetable, such as beetroot, effectively mixed with a salt content at a specified ratio. The enhanced food composition has the effect to prevent an increase in blood pressure while masking the bad taste of the nitrate-containing vegetable.

9 Claims, 1 Drawing Sheet

Figure 1
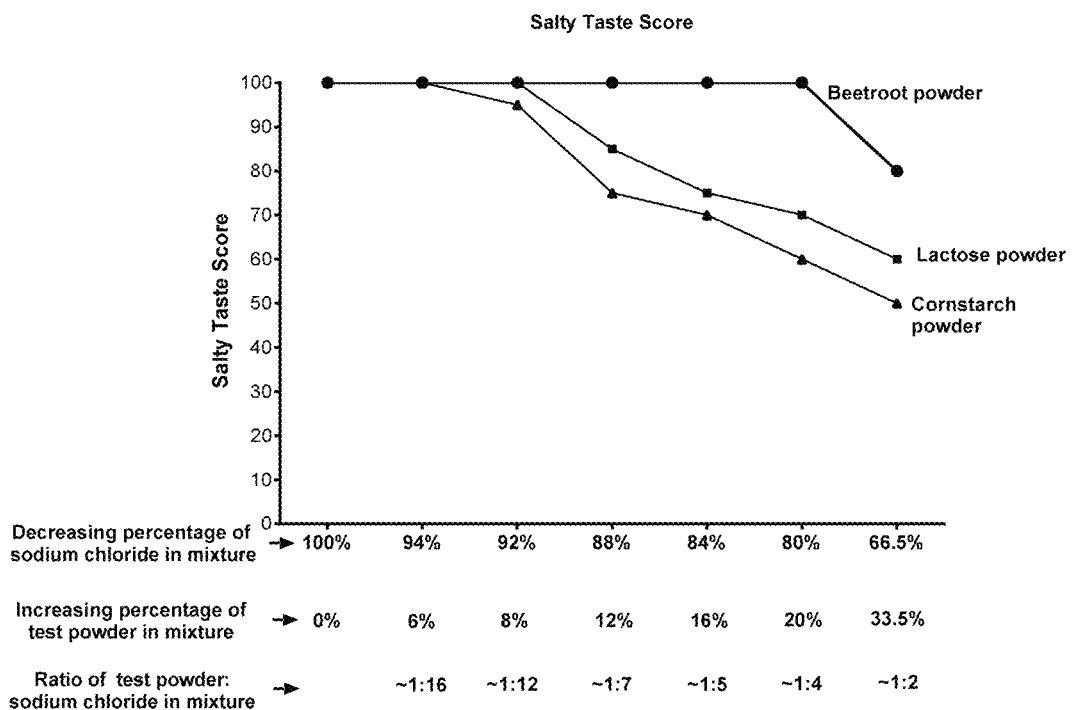
Figure 2
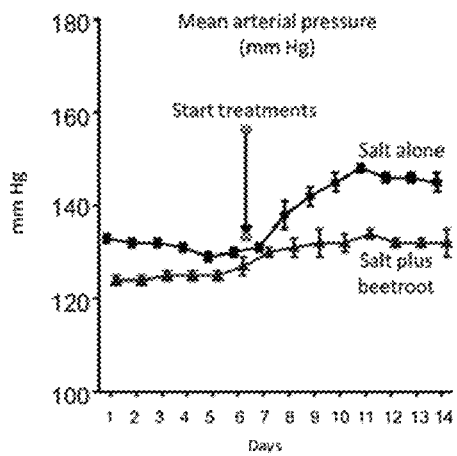
Fig 2(a)
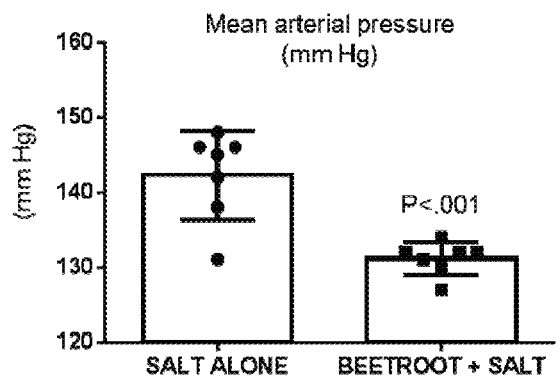
Fig 2(b)

BEETROOT-CONTAINING COMPOSITION

FIELD OF THE INVENTION

The present invention relates to a composition comprising beetroot, and a salty taste composition, food composition, composition for preventing increase in blood pressure, and so on, each comprising beetroot.

TECHNOLOGICAL BACKGROUND

Hypertension is a leading cause of cardiovascular morbidity and mortality in Japan and throughout the world. Hypertension (high blood pressure) is traditionally defined as a systolic blood pressure (SBP) equal to or greater than 140 mmHg and/or a diastolic blood pressure (DBP) equal to or greater than 90 mmHg. The term "prehypertension", as a pre-stage of hypertension, has been traditionally defined as a SBP of 120-139 mmHg and/or a DBP of 80-89 mmHg. Herein we use the traditional definitions of hypertension and prehypertension. Prehypertension is a very strong predictor of hypertension. In Japan, approximately 40% of adults over 60 years old are considered to have prehypertension. Blood pressure increases with age and the prevalence of hypertension in Japanese people who are 60 years or older is more than 60% and is also very high in other elderly populations. For example, in the United States, over 65% of people greater than 65 years of age have hypertension as traditionally defined (see https://www.cdc.gov/bloodpressure/facts.htm).

Approximately 50% of people with hypertension and approximately 25% of people with normal blood pressure experience increased blood pressure in response to excessive salt (sodium chloride) intake (Elijovich F, Weinberger M H, Anderson C A et al. Salt Sensitivity of Blood Pressure: A Scientific Statement From the American Heart Association. Hypertension 2016; 68:e7-e46). Salt-sensitivity is defined as a condition in which increases in salt intake induce increases in blood pressure. Thus, approximately 50% of people with hypertension are salt-sensitive (have salt-sensitivity) and approximately 25% of people with normal blood pressure are salt-sensitive (have salt-sensitivity) (Elijovich F, Weinberger M H, Anderson C A et al. Salt Sensitivity of Blood Pressure: A Scientific Statement From the American Heart Association. Hypertension 2016; 68:e7-e46). Salt-sensitivity is a risk factor for hypertension, cardio- and cerebrovascular disorders, and an altered inflammatory immune response—the latter being linked to all major human diseases.

Many drugs have been approved for treatment of hypertension but not for treatment of prehypertension or salt-sensitivity. Thus, lifestyle changes including restriction of salt intake and weight loss are often recommended to decrease the incidence of prehypertension or hypertension.

Although many methods are known and available for decreasing the incidence of prehypertension or hypertension or cardiovascular diseases and metabolic disorders related thereto, the methods are often inconvenient and associated with side effects, or are not optimally effective. While dietary salt restriction is recommended to decrease the incidence of hypertension or the like and cardiovascular diseases or the like related thereto, people enjoy the taste of salt and consume more salt than the amount recommended by health authorities. For example, the Japanese Society of Hypertension recommends to consume less than 6 grams of salt (sodium chloride) per day. However, adults in Japan consume an average of about 10 g of salt per day. Average salt intake in most populations worldwide is approximately 9 grams per day and other medical societies throughout the world also recommend reducing salt intake to well below that level. The World Health Organization recommends consumption of less than approximately 5 grams of salt per day and the American Heart Association recommends no more than 3.8 grams of salt per day. However, many if not most individuals continue to consume approximately 9-10 grams of salt per day. Thus, there is an unmet need for safe, well tolerated, and practical methods for decreasing the incidence of prehypertension or hypertension caused by excessive salt intake or other mechanisms.

Foods with functional characteristics represent a promising and safe approach for decreasing the incidence of prehypertension or hypertension. In Japan, for example, the government has approved a variety of foods with functional characteristics that are useful in maintaining normal blood pressure as "food for specialized health uses", "food with function claims", etc. Other governments such as in the United States have also approved the fortification of food products with added natural ingredients that are beneficial for health.

It is well-established that beet plant-derived products including beetroot juice and beetroot powder can be used to reduce blood pressure in individuals with hypertension or individuals with normal blood pressure, or to decrease the incidence of hypertension (Jonvic K L et al "Nitrate-Rich Vegetables Increase Plasma Nitrate and Nitrite Concentrations and Lower Blood Pressure in Healthy Adults." J Nutr. 2016 May; 146 (5): 986-93. Kapil V et al "Dietary Nitrate Provides Sustained Blood Pressure Lowering in Hypertensive Patients: a randomized, phase 2, double-blind, placebo-controlled study." Hypertension 2015 February; 65 (2): 320-327). The anti-hypertensive effect of beet plant-derived products is related mainly to the high concentration of inorganic nitrate in beetroot, which is converted in the body to nitric oxide, a potent vasodilating agent that relaxes blood vessels and reduces blood pressure (Gee L C, Ahluwalia A. Dietary Nitrate Lowers Blood Pressure: Epidemiological, Pre-clinical Experimental and Clinical Trial Evidence. Curr Hypertens Rep. 2016; 18:17). Recently, it has become evident that reduced nitric oxide activity causes salt-sensitivity and that dietary-induced increases in nitric oxide activity can prevent salt-induced increases in blood pressure (Fujiwara N, Osanai T, Kamada T, Katoh T, Takahashi K, Okumura K. Study on the relationship between plasma nitrite and nitrate level and salt sensitivity in human hypertension: modulation of nitric oxide synthesis by salt intake. Circulation. 2000; 101:856-61. Chen P Y, Sanders P W. L-arginine abrogates salt-sensitive hypertension in Dahl/Rapp rats. J Clin Invest. 1991; 88:1559-67. Carlstrom M, Persson A E, Larsson E, Hezel M, Scheffer P G, Teerlink T, et al. Dietary nitrate attenuates oxidative stress, prevents cardiac and renal injuries, and reduces blood pressure in salt-induced hypertension. Cardiovasc Res. 2011; 89:574-85. Morris R C, Schmidlin O, Sebastian A, Tanaka M, Kurtz T W. Vasodysfunction that involves renal vasodysfunction, not abnormally increased renal retention of sodium, accounts for the initiation of salt-induced hypertension. Circulation. 2016; 133:881-93).

Safe amounts of inorganic nitrate that can reduce blood pressure and decrease the incidence of prehypertension or hypertension can be obtained through dietary means by consuming vegetables like beetroot with high nitrate content (Jonvic K L et al "Nitrate-Rich Vegetables Increase Plasma Nitrate and Nitrite Concentrations and Lower Blood Pressure in Healthy Adults." J Nutr. 2016 May; 146 (5): 986-93.

Kapil V et al "Dietary Nitrate Provides Sustained Blood Pressure Lowering in Hypertensive Patients: a randomized, phase 2, double-blind, placebo-controlled study." Hypertension 2015 February; 65 (2): 320-327). In addition to beetroot, there are many other vegetables that contain substantial amounts of inorganic nitrate, and products derived from such vegetables can also be useful for treating prehypertension and hypertension, or decreasing an incidence of such a disorder through a similar mechanism (Sobko T et al "Dietary nitrate in Japanese traditional foods lowers diastolic blood pressure in healthy volunteers." Nitric Oxide. 2010 Feb. 15; 22(2):136-40).

However, many individuals do not like the taste of beetroot in general because it contains pyrazine compounds and a large amount of geosmin ((4S,4aS,8aR)-4,8a-dimethyl-1, 2,3,4,5,6,7-octahydronaphthalen-4a-ol), an organic compound that has an earthy flavor.

SUMMARY OF INVENTION

To provide a beet plant-containing composition that is more palatable for consumption and is useful for preventing an increase in blood pressure, it is required to reduce or remove the bad taste of geosmin and the like in beetroot. However, the processes, for example, required to remove geosmin and other bad-tasting compounds from beetroot are often time-consuming, complex, and expensive. No suitable method has been previously known which is capable of masking or neutralizing the earthy taste of beetroot in the desired fashion. When seeking substances to mask or neutralize the earthy taste of beetroot in compositions comprising beetroot, consideration should be given to both the palatability of such compositions and their capacity to protect against increases in blood pressure.

In view of the limitations of the above conventional techniques, a purpose of the present invention is to provide a beet plant-containing composition that is without the bad taste of beetroot and that is useful for preventing an increase in blood pressure. An additional purpose is to provide an antihypertensive composition containing beetroot that enhances the antihypertensive activity of beetroot and also has improved taste.

Use of a seasoning product or seasoning agent that does not contain salt, or that contains some salt diluted by addition of other ingredients, is often recommended as a means to avoid a salt-induced increase in blood pressure and to decrease an incidence of prehypertension or hypertension. Such seasoning products or seasoning agents are sometimes referred to as salt substitutes. However, many such seasoning products that do not contain salt, or that contain some salt diluted by addition of other ingredients, typically lack a sufficient salty taste or have an unpleasant, bitter or chemical taste, and are not palatable.

In view of the limitations of the above conventional techniques, another purpose of this invention is to provide salty taste compositions, and salty taste compositions for reducing risk for an increase in blood pressure, that are palatable and have an enhanced salty taste.

By seasoning food with the novel salty taste compositions of this invention, instead of seasoning food with ordinary salt or ordinary salty taste compositions, one can reduce the amount of salt consumed without reducing the salty taste of the food. Moreover, because the novel salty taste compositions have antihypertensive properties, the amount of salt present in the compositions does not increase the risk for hypertension. Thus, use of the novel salty taste compositions in place of ordinary salt affords two major benefits with respect to protecting against salt-induced hypertension: 1) reducing the amount of salt consumed without a reduction in salty taste, and 2) preventing the salt that is consumed from increasing a risk for increased blood pressure. Use of the novel salty taste compositions in place of other salty taste compositions containing reduced amounts of salt also affords major benefits: 1) reducing the amount of salt consumed without reducing a salty taste and without causing a bad taste, and 2) preventing the salt that is consumed in the composition from increasing a risk for increased blood pressure. Thus, purposes of this invention include providing a palatable salty taste-imparting agent, and a palatable salty taste imparting agent useful for reducing a risk for a salt-induced increase in blood pressure.

The present inventor conducted intensive research to attain the above purposes, and surprisingly found that salt, or one or more additional food materials selected from the group consisting of fruits of the family Rutaceae, vegetables of the family Brassicaceae, and vegetables of the family Amaranthaceae, can have the effect to mask the earthy taste of beetroot. Further, the inventor surprisingly found that beetroot mixed with salt can act as a salty taste enhancer and be used to prepare palatable salty taste compositions that have an enhanced salty taste and that contain beetroot in amounts that can reduce the risk for a salt-induced increase in blood pressure, and thus completed the present inventions.

Specifically, the present invention includes the following configurations.

(1) A salty taste composition comprising beetroot and salt, wherein the composition comprises 5 to 30% by dry weight of the beetroot and 70 to 95% by dry weight of the salt based on the total weight of the composition.

(2) A salty taste composition comprising beetroot and salt, wherein the ratio of the beetroot to the salt (beetroot:salt) by dry weight in the composition is 1:16 to 1:4.

(3) The salty taste composition (2), wherein the ratio of the beetroot to the salt (beetroot:salt) by dry weight in the composition is 1:16.

(4) The salty taste composition in any one of (1) to (3), wherein the composition comprises an additional food material.

(5) The salty taste composition described in any one of (1) to (4), wherein the additional food material comprises at least one or more nitrate-containing food materials.

(6) The salty taste composition described in any one of (1) to (5), wherein the additional food material comprises Vitamin D and/or vitamin C (7) The salty taste composition described in any one of (1) to (6), for a human with hypertension or prehypertension.

(8) A food composition comprising the salty taste composition described in any one of (1) to (7).

(9) The food composition of (8), being soy sauce (shoyu).

(10) A composition comprising beetroot and salt for preventing a salt-induced increase in blood pressure, wherein the composition comprises 5 to 30% by dry weight of the beetroot and 70 to 95% by dry weight of the salt based on the total weight of the composition.

(11) A composition comprising beetroot and salt for preventing a salt-induced increase in blood pressure, wherein the ratio of the beetroot to the salt (beetroot:salt) by dry weight in the composition is 1:16 to 1:4.

(12). The composition of (11), wherein the ratio of the beetroot to the salt (beetroot:salt) by dry weight in the composition is 1:16.

(13) The composition of (10) to (12), comprising an additional food material.

(14) The composition described in any one of (10) to (13), wherein the additional food material comprises at least one or more nitrate-containing food materials.
(15) The composition described in any one of (10) to (14), wherein the additional food material comprises Vitamin D and/or a supplement of vitamin D.
(16) A method for preventing an increase in blood pressure, the method comprises administering the composition described in any one of (1) to (7) to (10) or (10) to (15) to a human with prehypertension.
(17) A method for preventing or treating salt-induced hypertension, wherein the composition described in (7) to (10) or (10) to (15) is used as a salt substitute.
(18) A method for enhancing a salty taste of a composition containing salt, comprising substituting the salt of the composition with beetroot in an amount of 5 to 30% by dry weight of beetroot based on the weight of the salt to be added.
(19) A method for enhancing a salty taste of a composition containing salt, comprising adding beetroot to the composition with the ratio of the beetroot to the salt (beetroot:salt) by dry weight in the composition is 1:16 to 1:4.
(20) The method described in (19), wherein the ratio of the beetroot to the salt (beetroot:salt) by dry weight in the composition is 1:16.
(21) The method described in any one of (18) to (20), wherein the composition comprises an additional food material.
(22) The method described in any one of (18) to (21), wherein the additional food material comprises at least one or more nitrate-containing food materials.
(23) The method described in any one of (18) to (22), wherein the additional food material comprises Vitamin D and/or vitamin C
(24) A method for preventing an increase in blood pressure by using a salty taste composition having an enhanced salty taste, the method comprises: providing the salty taste composition containing beetroot in an amount (dry weight) of 5 to 30% by dry weight of the salt; and consuming the salty taste composition by a human with hypertension or prehypertension in place of the salt.
(25) A method for preventing an increase in blood pressure by using a salty taste composition having an enhanced salty taste, the method comprises: providing the salty taste composition containing beetroot and salt such that the ratio of beetroot to salt (beetroot:salt) by dry weight in the composition is 1:16 to 1:4; and
consuming the salty taste composition by a human with hypertension or prehypertension in place of the salt.
(26) The method described in (25), wherein the ratio of beetroot to salt (beetroot:salt) by dry weight in the composition is 1:16.
(27) The salty taste composition described in any one of (1) to (7) or the composition described in any one of (10) to (15), wherein the beetroot in the composition is in the form of powder, granules, or crystalline particles and the salt in the composition is in the form of powder, granules, or crystalline particles, and the composition is a powder composition as a mixture of the beetroot and the salt.

The present invention further includes the following configurations.
[1] A salty taste composition comprising beetroot and salt.
[2] The salty taste composition of [1], comprising 20 to 65% by dry weight of the beetroot and 35 to 80% by dry weight of the salt.
[3] The salty taste composition of [1] or [2], wherein the ratio of the beetroot to the salt by dry weight in the composition is 0.6:1 to 1.8:1.
[4] The salty taste composition described in any one of [1] to [3], wherein the salty taste composition comprises an additional food material, and the total content of the beetroot and the salt is 20 to 90% by dry weight, and the content of the additional food material is 10 to 80% by dry weight in the composition.
[5] The salty taste composition described in any one of [1] to [4], wherein the additional food material comprises at least one or more nitrate-containing food materials.
[6] The salty taste composition described in any one of [1] to [5], wherein the additional food material comprises at least one or more seasonings.
[7] The salty taste composition described in any one of [1] to [6], wherein the additional food material comprises a supplement of vitamin D and or other vitamins
[8] The salty taste composition described in any one of [1] to [7], wherein the beetroot in the composition is in the form of powder, granules, or crystalline particles and the salt in the composition is in the form of powder, granules, or crystalline particles, and the composition is a powder composition as a mixture of the beetroot and the salt.
[9] The salty taste composition described in any one of [1] to [8], for a human with rather high blood pressure.
[10] A salty taste composition for preventing an increase in blood pressure, the composition comprising beetroot and salt.
[11] The salty taste composition for preventing an increase in blood pressure of [10], the composition comprising 20 to 65% by dry weight of the beetroot and 35 to 80% by dry weight of the salt.
[12] The salty taste composition for preventing an increase in blood pressure of [10] or [11], wherein the ratio of the beetroot to the salt by dry weight in the composition is 0.6:1 to 1.8:1.
[13] The salty taste composition for preventing an increase in blood pressure described in any one of [10] to [12], wherein the total content of the beetroot and the salt is 20 to 90% by dry weight, and the content of an additional food material is 10 to 80% by dry weight in the composition.
[14] The salty taste composition for preventing an increase in blood pressure described in any one of [10] to [13], wherein the additional food material comprises at least one or more nitrate-containing food materials.
[15] The salty taste composition for preventing an increase in blood pressure described in any one of [10] to [14], wherein the additional food material comprises at least one or more seasonings.
[16] The salty taste composition for preventing an increase in blood pressure described in any one of [10] to [15], wherein the additional food material comprises a supplement of vitamin D and or other vitamins.
[17] The salty taste composition for preventing an increase in blood pressure described in any one of [10] to [16], wherein the beetroot in the composition is in the form of powder, granules, or crystalline particles and the salt in the composition is in the form of powder, granules, or crystalline particles, and the composition is a powder composition as a mixture of the beetroot and the salt.
[18] The salty taste composition for preventing an increase in blood pressure described in any one of [10] to [17], for a human with rather high blood pressure.
[19] A salty taste-imparting agent comprising beetroot and salt as active ingredients.

[20] A salty taste enhancer comprising beetroot as an active ingredient.
[21] A food composition comprising the salty taste composition described in any one of [1] to [18].
[22] The food composition of [21], being soy sauce (shoyu).
[23] An anti-hypertension composition, the composition comprising beetroot and further comprising one or more additional food materials selected from the group consisting of fruits of the family Rutaceae, vegetables of the family Brassicaceae, and vegetables of the family Amaranthaceae in an effective amount for masking the taste of the beetroot.
[24] The anti-hypertension composition of [23], for administering to a human with hypertension.
[25] The anti-hypertension composition of [23], for administering to a human with prehypertension.
[26] The anti-hypertension composition of [23], for administering to a human with normal blood pressure.
[27] The anti-hypertension composition described in any one of [23] to [26], to be formulated as a form of a powder, granule, tablet, liquid, capsule, troche, or jelly.
[28] The anti-hypertension composition described in any one of [23] to [27], wherein the additional food material is one or more selected from the group consisting of shikuwasa, yuzu, komatsuna, ging-gen-cai, and spinach.
[29] The anti-hypertension composition described in any one of [23] to [27], the composition comprising 0.1 to 10 parts by mass of the additional food material with respect to 1 part by mass of the beetroot, in terms of dry solid content.
[30] The anti-hypertension composition described in any one of [23] to [29], for administering the beetroot in an amount of 0.5 to 10 g in terms of dry solid content per day.
[31] The anti-hypertension composition described in any one of [23] to [30], to be mixed in 100 mL to 1000 mL of liquid to prepare a liquid composition comprising the beetroot and the additional food material.
[32] The anti-hypertension composition described in any one of [23] to [31], to be contained in a unit dose package so that 0.5 g to 10 g of the beetroot in terms of dry solid content is contained in the package.
[33] The anti-hypertension composition described in any one of [23] to [32], to be contained in a unit dose package so that 0.5 g to 10 g of the beetroot in terms of dry solid content is contained in the package and 0.5 to 10 g of the additional food material in terms of dry solid content is contained in the package.

In some embodiments, the present invention provides an anti-hypertension composition comprising beetroot and salt with additional food materials that enhance the antihypertensive activity of beetroot and also reduce the bad taste of beetroot.

In addition, the present invention can provide a salty taste composition and salty taste composition for preventing an increase in blood pressure by the combination of beetroot and salt, wherein the salt masks the earthy taste of the beetroot and the beetroot enhances the salty taste of the salt, each of the compositions having enhanced salty taste, being palatable, without deterioration of salty taste in spite of the reduced amount of salt, and also being excellent in the effect to prevent increase in blood pressure. The present invention can also provide a salty taste-imparting agent, and a salty taste enhancer useful for preventing an increase in blood pressure.

The composition of the present invention can contain, in addition to beetroot, for example, one or more additional food materials selected from the group consisting of fruits of the family Rutaceae, nitrate containing vegetables of the family Brassicaceae, or nitrate containing vegetables of the family Amaranthaceae. By virtue of this configuration, a food composition can be provided with the earthy taste of beetroot masked and the anti-hypertensive activity of beetroot more enhanced.

BRIEF DESCRIPTION OF THE DRAWINGS

FIG. 1 illustrates the effect of beetroot powder and other powders to salty taste.

FIG. 2(a) illustrates 24-hour mean arterial pressures measured by radiotelemetry before and after initiating two treatments.

FIG. 2(b) illustrates the comparison of blood pressures between the treatment with beetroot and salt and the treatment with salt alone.

DETAILS DESCRIPTION OF EMBODIMENTS

The beetroot-containing composition according to the present invention comprises beetroot, and further comprises one or more food materials to mask the taste of the beetroot.

Examples of the food materials to mask the taste of beetroot include, as shown in Examples below, salt, fruits of the family Rutaceae such as shikuwasa and yuzu, and nitrate containing vegetables of the family Brassicaceae such as komatsuna and ging-gen-cai, and nitrate containing vegetables of the family Amaranthaceae such as spinach.

Beet (*Beta vulgaris*), which is known as a root vegetable, is a plant that belongs to Amaranthaceae, Chenopodiaceae, Beta, and popular examples thereof include sugar beet, red beet, table beet, beets, *Beta vulgaris*, and garden beet.

The term "beet" as used herein means any part of the beet plant that contains nitrate including the root, leaves, bark etc. with the root being the preferred part for purposes of this invention. The root may include other parts of the plant body such as the root bark. Examples of the beetroot include, but are not limited to, Red beetroot, Golden or gold beetroot, Yellow beetroot, and White beetroot Albino, each currently cultivated; the native species (white root) "Bull's Blood"; the native species "Chioggia"; the native species (distinct red and white zoned root) "Crosby's Egyptian"; the native species "Cylindra"/"Formanova"; the native species (elongated root) "Detroit Dark Red Medium Top"; the native species "Early Wonder"; the native species "Golden Beet"/"Burpee's Golden"; the native species (yellow root) "Perfected Detroit", "Red Ace"; and the hybrid "Ruby Queen", "Touchstone Gold" (yellow root). Alternatively, beetroot developed or genetically modified so as to contain inorganic nitrates, which are converted into nitric oxide in the body, in an amount larger than those contained in conventional varieties may be used in the present invention. The term "beetroot" is defined to mean all types of beetroot including any member of the group *Beta vulgaris* such as the above-mentioned ones.

The term "beetroot" includes all forms. For example, the form can be a dry powder prepared, for example, through directly freeze-drying or spray-drying a natural material of a root, including the root and the root bark, in order to use natural, useful components. Also, squeezed juice or grounded paste from the material may be used. Also, an extract, for example, extracted from a raw material with a solvent such as water added thereto can be used. Beetroot products of food grade from any source can be suitably used in the present invention.

Herein, the term "salt" refers to any form of sodium chloride alone and a combination of sodium chloride and other inorganic salts in which the sodium chloride accounts for 50% or more of the ingredient salts on a weight basis or molar basis. The term "salt" also includes rock salt, sea salt, and flavored salt such as soy salt, garlic salt, and celery salt. The term "salt" is also intended to include salt materials of any size including coarse, fine, extra fine, and micro-fine salts, and salts of other sizes. Sodium chloride of food grade from any source can be suitably used in the present invention.

The present invention provides a salty taste composition comprising the above-explained beetroot and salt. In a preferred embodiment of the present invention, the salty taste composition comprises 5 to 65% by dry weight of beetroot, based on the total weight of the salty taste composition, and almost all of the rest of the salty taste composition consists of salt. Hence, in this case, the salty taste composition comprises 35 to 95% by dry weight of salt. Here, the "% by dry weight" used in the specification means the % ratio based on the total weight of the salty taste composition In a more preferred embodiment of the present invention, the salty taste composition comprises 5 to 60% by dry weight of beetroot, and almost all of the rest of the salty taste composition consists of salt. Hence, in this case, the salty taste composition comprises 40 to 95% by dry weight of salt. Particularly preferably, the salty taste composition comprises 5 to 30% by dry weight of beetroot. The most preferably, the salty taste composition comprises 5 to 25% by dry weight of beetroot. In a preferred embodiment of the present invention, the ratio of beetroot to salt by dry weight in the salty taste composition is 0.6:1 to 1.8:1, and is 0.8:1 to 1.5:1 in a more preferred embodiment. Alternatively, the ratio of beetroot to salt by dry weight in the salty taste composition is 1:16 to 1:4, and is 1:16 to 1:8 in a more preferred embodiment. As demonstrated later in Examples, if the amount of beetroot is excessively large with respect to that of salt, the salty taste composition will lack salty taste, and it will be difficult to obtain the effect of salt to mask the earthy taste of beetroot. If the amount of beetroot is excessively small with respect to that of salt, the salty taste composition will lack the effect to enhance the salty taste of salt, and it will be difficult to obtain the effect of beetroot to prevent salt-induced increases in blood pressure.

In some embodiments, the salty taste composition can be comprised of salt together with nitrate-containing vegetable matter without beetroot in the composition, provided that the nitrate-containing vegetable matter provides a ratio of nitrate:salt in the composition of 1:160 or greater, as such ratios of nitrate:salt are sufficient to reduce a risk for salt-induced increases in blood pressure (see Carlstrom M, Persson A E, Larsson E, Hezel M, Scheffer P G, Teerlink T, et al. Dietary nitrate attenuates oxidative stress, prevents cardiac and renal injuries, and reduces blood pressure in salt-induced hypertension. Cardiovasc Res. 2011; 89:574-85; and also see FIG. 2 herein). Examples of such nitrate-containing vegetables that can provide adequate amounts of nitrate similar to those provided by beetroot are shown in Table 1.

The salty taste composition comprised of beetroot and salt according to the present invention can contain, in addition to the above-explained beetroot and salt, an additional food material, without interfering with the effect of the present invention. In this case, it is preferred that the total content of beetroot and salt be 20 to 90% by dry weight and the content of the additional food material be 10 to 80% by dry weight in the salty taste composition, and it is more preferred that the total content of beetroot and salt be 50 to 90% by dry weight and the content of the additional food material be 10 to 50% by dry weight in the salty taste composition, based on the total weight of the salty taste composition. If the content of the additional food material is excessively large with respect to the total content of beetroot and salt in the salty taste composition, the salty taste composition may lack salty taste. Here, the composition of the present invention means having an enhanced salty taste in comparison to a composition in which beetroot of the present composition is substituted with other ingredients. The "enhanced salty taste" means a salty taste practically equivalent to that of a salt-containing composition in which the beetroot component of the salty taste composition is substituted with salt, or a greater salty taste than that of a salt-containing composition in which the beetroot component is substituted with some other ingredient.

Examples of the additional food material include a nitrate-containing food material. The nitrate-containing food material can provide a salty taste composition having more excellent effect to prevent an increase in blood pressure, by virtue of the action of nitric oxide generated in the body from the nitrate-containing food material concomitant with nitric oxide generated in the body from the beetroot, which is similarly a nitrate-containing food material. As mentioned above, nitric oxide is a vasodilator that relaxes blood vessels and reduces blood pressure. Recently, it has become evident that reduced nitric oxide activity causes salt-sensitivity and that increased nitric oxide activity prevents salt-induced increase in blood pressure.

Shikuwasa as used in the present invention refers to the fruit of shikuwasa, which is known as a citrus fruit. The term "fruit" may include the pericarp, and the like. Shikuwasa (*Citrus depressa*) is a plant of the genus *Citrus* of Rutaceae, and sometimes called Hirami Lemon as the Japanese name. The production area of shikuwasa is not limited for the purpose of use in the present invention.

Yuzu as used in the present invention refers to the fruit of yuzu, which is known as a citrus fruit. The term "fruit" may include the pericarp. Yuzu (*Citrus junos*) is a plant of the genus *Citrus* of Rutaceae. Yuzu is not limited to the specific species for the purpose of use in the present invention.

Komatsuna as used in the present invention refers to the leaf of komatsuna, which is known as a leaf vegetable. The term "leaf" may include the stem and root. Komatsuna (*Brassica rapa* var. *perviridis*) is a plant of the genus *Brassica* of Brassicaceae. The production area of komatsuna is not limited for the purpose of use in the present invention.

Ging-gen-cai as used in the present invention refers to the leaf of ging-gen-cai, which is known as a leaf vegetable. The term "leaf" may include the stem and root. Ging-gen-cai (*Brassica rapa* var. *chinensis*) is a plant of the genus *Brassica* of Brassicaceae, which is sometimes called Taisai as the Japanese name. The production area of ging-gen-cai is not limited for the purpose of use in the present invention.

Spinach as used in the present invention refers to the leaf of spinach, which is known as a leaf vegetable. The term "leaf" may include the stem and root. Spinach (*Spinacia oleracea*) is a plant of the genus *Spinacia* of Chenopodioideae of Amaranthaceae. The production area of spinach is not limited for the purposes of use in the present invention.

In addition to the above-mentioned fruits of the family Rutaceae such as shikuwasa and yuzu, vegetables of the family Brassicaceae such as komatsuna and ging-gen-cai, and vegetables of the family Amaranthaceae such as spinach, a known food material, for example, and any of nitrate-rich vegetables listed in Table 1 below can be appropriately selected for use as the nitrate-containing food material. In Table 1, Chinese cabbage is known as komatsuna in Japan. Rocket is also known as rucola or arugula. One nitrate-containing food material or two or more nitrate-containing food materials may be used. Nitrate-containing food materials of food grade from any source can be suitably used in the present invention.

TABLE 1

| Vegetable with high nitrate content | Mean nitrate content [range] (mg/kg) |
|---|---|
| Rocket | 2597 [0033] |
| Spinach | 2137 [965-4259] |
| Lettuce | 1893 [970-2782] |
| Radish | 1868 [1060-2600] |
| Beetroot | 1459 [644-1800] |
| Chinese cabbage | 1388 [1040-1859] |

This Table showing vegetables with high nitrate content is taken from "Vascular effects of dietary nitrate (as found in green leafy vegetables and beetroot) via the nitrate-nitrite-nitric oxide pathway", Lidder S, Webb A J. Br. J Clin. Pharmacol. 2013 March; 75(3):677-96 (Excerpt).

The composition according to the present invention can further contain a food material other than the above-explained food materials, without interfering with the effect of the present invention. Examples thereof include food materials listed in Table 2 below. Any form may be appropriately selected for those food materials, and examples thereof include powder, crystals, crystalline particles, concentrates, juices, and derivatives thereof.

TABLE 2

| | |
|---|---|
| Kyoho | Persimmon |
| Shikuwasa | Hirome (*Undaria undarioides*) |
| Yuzu | Mekabu |
| Satonishiki | Agar |
| Japanese apricot | Arame (*Eisenia bicyclis*) |
| Kabosu | Badderlocks (*Alaria esculenta*) |
| Kinkan | Cochayuyo (*Durvillaea antarctica*) |
| Daidai | *Ecklonia cava* (*Ecklonia cava*) |
| Sudachi | Oarweed (*Laminaria digitata*) |
| Green tea | Sugar kelp (*Saccharina latissima*) |
| Hashouga | Wakame (*Undaria pinnatifida*) |
| Ginger | Salt |
| Myouga | Moshio |
| Wasabi | |
| Miso | |
| Hijiki | |
| Iwanori | |
| Nori | |
| Ao-nori | |
| Kombu (*Saccharina japonica*) | |

Each of the above food materials can be used as an additive for the salty taste composition comprising beetroot. Each of the above food materials including shikuwasa, yuzu, komatsuna, ging-gen-cai, and spinach concomitantly, have the effect to enhance the anti-hypertensive activity of beetroot. The mechanism of the anti-hypertensive activity is considered to be related to increase of the nitric oxide-producing activity, as with the case of beetroot. The beneficial effect is achieved by providing additional nitrate and or compounds that amplify the body's ability to generate nitric oxide from nitrate or other sources. In addition, each of these food materials can be used as a food material to mask the taste of beetroot.

In the case that any of the above food materials is used for masking the taste of beetroot, the amount suitable for masking in the anti-hypertensive composition according to the present invention can be determined by performing an appropriate sensory evaluation examination. Specifically, whether any of the above-mentioned food materials is contained in an effective amount for masking the bad taste of beetroot can be determined through an appropriate sensory evaluation examination with a plurality of panelists, where the taste of the anti-hypertensive composition according to the present invention is compared with the taste of an anti-hypertensive composition prepared with a formulation obtained by excluding the above-mentioned food materials for masking the bad taste of beetroot from the anti-hypertensive composition according to the present invention.

Herein, the term "masking" means decreasing the bad taste of beetroot, or changing it to a palatable taste, and does not necessarily mean decreasing the amount of the causal ingredients for the bad taste contained in beetroot. Rather "masking" means making it very difficult to detect in a sensory manner the bad taste, through mixing the ingredients conferring the bad taste with the other ingredients contained in the food materials for masking the bad taste.

The form of materials to be used in the present invention, including the food materials mentioned above such as beetroot, shikuwasa, yuzu, komatsuna, ging-gen-cai, and spinach, are not particularly limited in any manner. However, it is preferred to use a dry powder prepared, for example, through directly freeze-drying or spray-drying a natural material of a root or fruit in order to use natural, useful components directly. Also, squeezed juice or grounded paste from the material may be used. Also, an extract, for example, extracted from a raw material with a solvent such as water added thereto can be used. One food material for masking the taste of beetroot may be used, or a combination including two or more food materials therefor may be used.

Examples of the additional food material further include a seasoning. By virtue of the seasoning, the present invention can provide the salty taste composition with a unique scent and taste imparted thereto. Any of known seasonings for food, for example, listed in Table 3 below can be appropriately selected for use. One seasoning may be used, or two or more seasonings may be used. The seasoning may be contained or fabricated as an additional food material together with the nitrate-containing food material. Seasonings of food grade from any source can be suitably used in the present invention.

TABLE 3

| Name | Category |
|---|---|
| 18 Spice Chicken Rub | Dry Rub, Chicken Rubs |
| 8 Pepper Chili Seasoning | Chili Powder, Salt Free, Sugar Free |
| Achiote Seed | Caribbean |
| Adobo Lime Rub | Dry Rub, Chicken Rubs, Sugar Free |
| Adobo Seasoning | Caribbean, Salt Free, Sugar Free |
| Aji Panca Chile | Chiles and Hot Peppers |
| Ajwain Seed, Ground | Exotic |
| Al Pastor Taco Seasoning | Mexican, Sugar Free |
| Aleppo Pepper | Chile Flakes, Chiles and Hot Peppers |
| All American Dry Rub | Dry Rub, American |
| Allspice, Whole | Jamaican |
| Allspice Berries | Jamaican |
| Allspice, Ground | Jamaican |
| Amarillo Aji Chiles | Chiles & Hot Peppers |
| Amarillo Aji Chile Powder | Chiles & Hot Peppers |
| Amchur | Acidic Spices, Exotic |
| Anaheim Chiles, Dried | Chiles & Hot Peppers |
| Ancho Chiles, Dried | Chiles & Hot Peppers |
| Ancho Powder | Chiles & Hot Peppers |
| Andouille Sausage Seasoning | Sausage, Sugar Free |

TABLE 3-continued

| Name | Category |
|---|---|
| Anise Seed | Pickling Spice |
| Annato Seeds | Caribbean |
| Apple Pie Spice | Baking, Sugar Free |
| Applewood Chipotle Rub | Chicken Rubs |
| Arrowroot Powder | Baking |
| Asafoetida Powder | Baking |
| Austin Steak Rub | Beef Seasoning, Sugar Free |
| Bahamian Chicken | Caribbean, Chicken Rubs, Salt Free, Sugar Free |
| Baharat | African, Salt Free, Sugar Free |
| Barbacoa Rub | Dry Rub, Mexican |
| Basil, Sweet | Herbs |
| Bay Leaf | Herbs |
| Bay Leaf, Ground | Herbs |
| Beef Brisket Rub | Barbecue, American |
| Berbere | African, Sugar Free |
| Birdseye Chiles, Dried | Chiles & Hot Peppers |
| Birdseye Chile Powder | Chiles & Hot Peppers |
| Black Cumin | Earthy |
| Black & White Peppercorn Blend | Peppercorns, Sugar Free |
| Black Mustard Seed | Mustard, Exotic |
| Black Peppercorns | Peppercorns |
| Black Pepper, Coarse Grind | Pepper |
| Black Pepper, Medium Grind | Pepper |
| Black Pepper, Cracked | Pepper |
| Black Sesame Seeds | Nutty |
| Blackened Seasoning | Cajun & Creole, Sugar Free |
| Breakfast Sausage Seasoning | American, Sugar Free |
| Bourbon Molasses | Chicken Seasoning, Barbecue, Grill Seasonings |
| Brewpub Garlic Fries Seasoning | American, Sugar Free |
| Bristol Bay Salmon Seasoning | Salmon Seasoning, Sugar Free |
| Brown Mustard Seed | Mustard, Indian |
| Brown Mustard Seed Powder | Mustard, Indian |
| Brown Sugar, Light | Sugar |
| Buffalo Wing Rub | Dry Rub, American, Chicken Rubs |
| Butcher's Best Chicken Rub | Dry Rub, Chicken Rubs, Sugar Free |
| Burger Blast | American |
| Cacao Chile Rub | Dry Rub |
| Cacao Sugar | Baking |
| Cacao Powder | Baking |
| Cajun Rub (Hot) | Cajun & Creole, Dry Rub, Chicken Rubs, Sugar Free |
| Cajun Seasoning, Salt Free | Cajun & Creole, Salt Free, Sugar Free |
| Cajun Turkey Rub | Turkey, Cajun, Sugar Free |
| California Chiles, Dried | Chiles & Hot Peppers |
| Caraway Seed | Earthy |
| Cardamom Pods | Baking |
| Cardamom Seed | Baking |
| Cardamom Black Whole | Baking, Earthy |
| Cardamom Seed Powder | Baking |
| Caribbean Spice | Caribbean |
| Carolina Reaper Chile Flakes | Chiles & Hot Peppers, Chiles Flakes |
| Carolina Reaper Garlic Pepper | Pepper Blend, Sugar Free |
| Cascabel Chiles | Chiles & Hot Peppers |
| Cayenne Pepper (Hot 90,000 HU) | Chiles & Hot Peppers |
| Cayenne Pepper (Medium 35,000 HU) | Chiles & Hot Peppers |
| Celery Flakes | Vegetables |
| Celery Salt | Salt, Sugar Free |
| Celery Seed | Pickling Spice |
| Celery Seed Powder | Pickling Spice |
| Ceylon Cinnamon | Baking, Cinnamon |
| Ceylon Cinnamon Sticks 3" | Baking, Cinnamon |
| Chermoula Seasoning | African, Sugar Free |
| Chervil | Herbs |
| Chai Baking Spice Blend | Baking, Salt Free, Sugar Free |
| Chile Threads | Chiles & Hot Peppers |
| Chili Con Carne | Chili Powder, Salt Free, Sugar Free |
| Chili Lime Seasoning | South American, Sugar Free |
| Chili Powder, El Paso Hot | Chili Powder, Sugar Free |
| Chili Powder, Hill Country | Chili Powder, Sugar Free |
| Chili Powder Mild | Chili Powder, Salt Free, Sugar Free |
| Chili Powder, Sweet | Chili Powder, Salt Free |
| Chimichurri | South American, Salt Free, Sugar Free |
| Chinese Five Spice | Asian, Salt Free, Sugar Free |
| Chipotle Chiles, Dried | Chiles & Hot Peppers |
| Chipotle Flakes | Chiles & Hot Peppers |
| Chipotle Honey Rub | Dry Rub, Chicken Rubs |
| Chipotle "Meco" Chiles | Chiles & Hot Peppers |
| Chipotle "Morita" Chiles | Chiles & Hot Peppers, Chile Flakes |
| Chipotle "Meco" Powder | Chiles & Hot Peppers |
| Chipotle "Morita" Powder | Chiles & Hot Peppers |
| Chipotle Rub | Chiles & Hot Peppers, Dry Rub, Sugar Free |
| Chipotle Salt | Gourmet Salts, Sugar Free |
| Chives | Herbs |
| Chocolate Habanero Chiles | Chiles & Hot Peppers |
| Chop House Burger Seasoning | Grill Seasonings, Sugar Free |
| Cilantro | Mexican |
| Cinnamon Chips | Cinnamon |
| Cinnamon Powder, Korintje | Cinnamon |
| Cinnamon Sticks 2.75", Cassia | Cinnamon |
| Cinnamon Sticks 2.75", Ceylon | Cinnamon |
| Citrus Seasoning | Seafood, American, Salt Free, Sugar Free |
| Citrus Steak | Steak, Sugar Free |
| Cloves, Ground | Baking |
| Cloves, Whole | Baking |
| Coarse Sea Salt | Gourmet Salt |
| Coconut Flakes | Baking |
| Colombo Powder | Curry, Caribbean |
| Coriander Seed | Pickling Spice |
| Coriander Seed, Indian | Pickling Spice |
| Coriander Seed Powder | Pickling Spice |
| Cow Tippin' Steak Seasoning | Steak Seasoning, Sugar Free |
| Cracked Fennel | Ground Spices |
| Cream of Tartar | Baking |
| Creole Seasoning | Cajun & Creole, Sugar Free |
| Crushed Habanero Flakes | Chiles & Hot Peppers, Chile Flakes |
| Crushed Maras Pepper | Chiles & Hot Peppers, Chile Flakes |
| Crushed Red Pepper Flakes | Chiles & Hot Peppers |
| Crushed Urfa Biber | Mediterranean, Chiles |
| Crystalized Ginger | Baking |
| Cubeb Berries | Pepper, African, Exotic |
| Cumin Seed | Earthy |
| Cumin Seed, Ground | Earthy |
| Curing Salt (Prague Powder #1) | Sausage Spices |
| Curing Salt (Prague Powder #2) | Sausage Spices |
| Curry Leaves | Earthy |
| Curry Powder, Sweet | Curry, Salt Free |
| Curry, Madras | Curry, Salt Free |
| Curry, Maharajah Style | Curry, Salt Free |
| Curry, Vindaloo | Curry, Salt Free |
| De Arbol Chiles | Chiles & Hot Peppers |
| De Arbol Chile Powder | Chili Powder |
| Deep South Dry Rub | Dry Rub |
| Deer Jerky Seasoning | Wild Game, Sugar Free |
| Demerara Sugar | Baking, Sugar |
| Diablo Burger Seasoning | Burger Seasonings, Beef Seasonings |
| Diced Green Bell Pepper | Vegetables |
| Diced Red Bell Pepper | Vegetables |
| Dill Seed | Pickling Spice |
| Dill Weed | Herbs |
| Domestic Paprika | Paprika |
| Dried Anaheim Chiles | Chiles & Hot Peppers |
| Dried Ancho Chilies | Chiles & Hot Peppers |
| Dried Birdseye Chiles | Chiles & Hot Peppers, African |
| Dried Chipotle Chiles | Chiles & Hot Peppers |
| Dried Fenugreek Leaves | Herbs, Indian |
| Dried Grapefruit Peel | Citrus Zest |
| Dried Habanero Chilies | Chiles & Hot Peppers |
| Dried New Mexico Chiles | Chiles & Hot Peppers |
| Dried Nora Chiles | Chiles & Hot Peppers |
| Dried Pasilla Chiles | Chiles & Hot Peppers |

TABLE 3-continued

| Name | Category |
|---|---|
| Dried Peperoncino Chiles | Chiles & Hot Peppers |
| Dried Poblano Powder | Chiles & Hot Peppers |
| Dried Puya Chiles | Chiles & Hot Peppers |
| Dried Rose Petals | Sweet Spices, Exotic |
| Dried Serrano Chiles | Chiles & Hot Peppers |
| Dried Shallots | Vegetables |
| Dry Mustard Powder, Yellow | Mustard |
| Dukkah | Middle Eastern, Sugar Free |
| El Paso Chili Powder Hot | Chili Powder, Salt Free, Sugar Free |
| Espresso Rub | Dry Rub |
| Epazote Leaves | Mexican |
| Fajita Seasoning | American, Mexican, Sugar Free |
| Fenugreek Leaves, Dried | Herbs, Indian |
| Fennel Pollen | Anise Herbs |
| Fennel Seed | Anise Herbs |
| Fennel Seed, Ground | Anise Herbs |
| Fenugreek Seed | Bitter |
| File Powder | Cajun & Creole |
| Filipino Pork Rub | Pork Rubs |
| Fines Herbes | Herbs, Salt Free, Sugar Free |
| Flippin' The Bird | Chicken Rubs |
| Fort Worth Burger Seasoning | American |
| Garam Masala | Curry, Salt Free, Sugar Free |
| Garlic Flakes, Roasted (California) | Garlic |
| Garlic Herb Seasoning | Garlic, Salt Free, Sugar Free |
| Garlic Granules (California) | Garlic |
| Garlic Granules, Roasted (California) | Garlic |
| Garlic Powder (California) | Garlic |
| Garlic Salt | Garlic, Salt, Sugar Free |
| Ghost Chiles | Chiles and Hot Peppers |
| Ginger Crystallized | Baking |
| Ginger Root Powder | Baking |
| Gourmet Peppercorn Mixer | Peppercorns, Sugar Free |
| Grade A1 Poppy Seed | Nutty |
| Grains of Paradise | Pickling Spice, Exotic, African |
| Granulated Garlic (California) | Garlic |
| Granulated Green Bell Pepper | Vegetables |
| Granulated Molasses | American, Sugar |
| Granulated Red Bell Pepper, Roasted | Vegetables |
| Greek Oregano | Herbs |
| Greek Seasoning | Mediterranean, Sugar Free |
| Green Peppercorns | Peppercorns |
| Grilled Salmon Seasoning | Seafood, Salmon Seasoning |
| Ground Ajwain | Bitter |
| Ground Allspice | Jamaican |
| Ground Anise | Pickling Spice |
| Ground Black Pepper Coarse Grind | Pepper |
| Ground Black Pepper Fine Grind | Pepper |
| Ground Black Pepper Medium Grind | Pepper |
| Ground Cloves | Baking |
| Ground Cumin | Earthy |
| Ground Fennel Seed | Anise Herbs |
| Ground Mediterranean Oregano | Herbs |
| Ground Rosemary | Herbs |
| Ground Thyme | Herbs |
| Ground White Pepper | Pepper |
| Ground Serrano | Chiles & Hot Peppers |
| Ground Sichuan Pepper | Asian, Ground Peppers |
| Guajillo Chile | Chiles & Hot Peppers |
| Guajillo Chile Flakes | Chile Flakes |
| Guajillo Chile Powder | Chili Powder |
| Gulf Coast Bay Seasoning | American, Sugar Free |
| Gumbo File Powder | Cajun & Creole |
| Habanero Chiles, Chocolate | Chiles & Hot Peppers |
| Habanero Chiles, Dried | Chiles & Hot Peppers |
| Habanero Flakes | Chiles & Hot Peppers |
| Habanero Garlic Pepper | Pepper Blend, Sugar Free |
| Habanero Hot Salt | Gourmet Salt, Sugar Free |
| Habanero Powder | Chili Powder |
| Habanero Mango Rub | Chicken Rubs, Sugar Free |
| Harissa | African, Salt Free, Sugar Free |
| Hawaiian Alaea Red Salt | Gourmet Salt |
| Hawaiian Black Salt | Gourmet Salt |
| Hickory Salt, Smoked | Gourmet Salt |
| Herbs de Provence | Herbs, Salt Free, Sugar Free |
| Hill Country Chili Powder | Chili Powder, Salt Free, Sugar Free |
| Himalayan Pink Salt | Gourmet Salt |
| Himalayan Salt Block | Gourmet Salt |
| Honey, Granulated | Dry Rub |
| Honey Habanero Rub | Chicken Rubs |
| Horseradish Powder | Pungent Spices |
| Hot Chinese Mustard Powder | Ground Spices, Mustard |
| Hot Italian Sausage Seasoning | Sausage, Sugar Free |
| Hungarian Paprika | Paprika |
| Indian Coriander Seed | Pickling Spice |
| Italian Seasoning | Italian, Salt Free, Sugar Free |
| Jalapeno Seasoning Salt | Gourmet Salt |
| Jalapeno Flakes | Chiles & Hot Peppers, Chile Flakes |
| Jalapeno Powder | Chiles & Hot Peppers |
| Jamaican Jerk Seasoning | Caribbean, Dry Rub |
| Jambalaya Seasoning | Cajun & Creole, Salt Free, Sugar Free |
| Japones Chiles | Chiles & Hot Peppers |
| Juniper Berries, Whole | Sweet Spices, Exotic |
| Kaffir Lime Leaves | Herbs, Exotic |
| Kansas City BBQ Rub | Dry Rub |
| Kansas City Steak Seasoning | Dry Rub, Steak Seasoning |
| Kickin' Chicken | Dry Rub, Chicken Rubs |
| Korean Beef Seasoning | Asian, Beef Seasoning |
| Korean Chile Flakes | Chiles & Hot Peppers, Asian, Chile Flakes |
| Korintje Cinnamon Powder | Cinnamon |
| Kosher Salt | Salt |
| La Kama | Moroccan, Sugar Free |
| Lavender | Herbs |
| Lebanese 7 Spice | Middle Eastern, Salt Free, Sugar Free |
| Lemon Peel | Baking |
| Lemon Pepper | Pepper Blend, Salt Free, Sugar Free |
| Lemongrass Powder | Asian |
| Light Brown Sugar | Sugar |
| Lime Zest | Citrus Zest |
| Lime Pepper | Salt Free, Sugar Free |
| Little Rock BBQ Rub | Dry Rub, Sugar Free |
| Long Pepper | Pepper, African |
| Louisiana Fish Seasoning | Cajun & Creole, Dry Rub, Sugar Free |
| Mace, Ground | Earthy |
| Madagascar Vanilla Beans | Vanilla |
| Madras Curry | Curry, Salt Free, Sugar Free |
| Maharajah Style Curry | Curry, Salt Free, Sugar Free |
| Manazanillo Mexican Seasoning | Mexican, Salt Free, Sugar Free |
| Maras Pepper, Crushed | Chiles & Hot Peppers, Middle Eastern |
| Marjoram Leaf | Herbs |
| Mayan Coco | Baking, Mexican |
| Mediterranean Dry Rub | Dry Rub, Chicken Rubs, Sugar Free |
| Mediterranean Oregano | Herbs |
| Memphis Style BBQ Rib Rub | Dry Rub, Salt Free, Sugar Free |
| Mexican Allspice Berries | Mexican, Whole Seeds & Berries |
| Mexican Mole Seasoning | Mexican, Salt Free |
| Mexican Oregano | Herbs |
| Mexican Seasoning, Manzanillo | Mexican, Salt Free, Sugar Free |
| Mexican Chorizo Seasoning | Mexican, Sugar Free |
| Mignonette Peppercorns | Peppercorns, Sugar Free |
| Milan Bread Dipping Seasoning | Mediterranean, Bread Dipping Seasoning, Sugar Free |
| Minced Onion | Onion |
| Mojo Seasoning | Caribbean, Salt Free, Sugar Free |
| Mitmita Spice | African, Salt Free, Sugar Free |
| Montreal Steak Spice | Steak Seasoning, Dry Rub, Sugar Free |
| Moroccan Chicken Spice Rub | Dry Rub, Chicken Rubs |
| Moroccan Vegetable Rub | Dry Rub, Sugar Free |
| Mulato Chiles, Dried | Chiles & Hot Pepper |
| Mulling Spice | American |
| Napa Valley Pepper | Pepper Blend, Salt Free, Sugar Free |
| Naples Seasoning | Italian, Salt Free, Sugar Free |
| Nashville Hot Chicken Seasoning | Chicken, American |
| New Mexico Chiles, Dried | Chiles & Hot Peppers |

TABLE 3-continued

| Name | Category |
|---|---|
| New Mexico Chile Powder | Chiles & Hot Peppers |
| New York Pizza Sauce Seasoning | Italian, Salt Free, Sugar Free |
| *Nigella* Seeds (Black Caraway) | Nutty, Exotic |
| Nori Flakes | Exotic, Superfoods |
| North Carolina BBQ Rub | Seasoning |
| Nutmeg | Baking |
| Nutmeg Powder | Earthy |
| Onion Granules | Onion |
| Onion Powder | Onion |
| Onion, Minced Roasted | Onion |
| Onion Powder, Toasted | Onion |
| Onion Soup Mix | Onion, Soup Blends |
| Orange Zest | Baking |
| Oregano, Mediterranean | Herbs |
| Oregano, Mexican | Herbs |
| Paella Seasoning | Spanish, Sugar Free |
| Panch Phoron (Bengali Five Spice) | Asian, Sugar Free |
| Paprika, Domestic | Paprika |
| Paprika, Hungarian | Paprika |
| Paprika, Smoked (Hot) | Paprika |
| Paprika, Smoked (Sweet) | Paprika |
| Parsley | Herbs |
| Pasilla Chiles, Dried | Chiles & Hot Peppers |
| Pasilla Chile Powder | Chiles & Hot Peppers |
| Pasilla de Oaxaca Chiles | Chiles & Hot Peppers |
| Pennsylvania Pepper | Pepper Blend, Salt Free, Sugar Free |
| Pepper, Lemon | Pepper |
| Pepper, Pennsylvania | Pepper, Salt Free, Sugar Free |
| Peppercorn Beef Rub | Dry Rub, Salt Free, Steak Seasoning, Sugar Free |
| Peppercorns, Black | Peppercorns |
| Peppercorns, Black & White Blend | Peppercorns |
| Peppercorns, Gourmet Mix | Peppercorns |
| Peppercorns, Green | Peppercorns |
| Peppercorns, Sichuan | Peppercorns, Asian |
| Peppercorns, Tellicherry | Peppercorns |
| Peppercorns, White | Peppercorns |
| Pequin Chiles | Chiles & Hot Peppers |
| Peruvian Kebab Seasoning | South American, Sugar Free |
| Pickling Spice | Pickling Spice, Sugar Free |
| Pineapple Seranno Rub | Chicken Seasonings, Pork Rubs, Fish Seasoning |
| Piri Seasoning | African, Sugar Free |
| Pizza Seasoning | Italian, Salt Free, Sugar Free |
| Pollo Asado | Chicken Rubs, Mexican Seasoning, Salt Free, Sugar Free |
| Poppy Seed Dutch Blue | Nutty |
| Pork Stank | Dry Rub |
| Poultry Seasoning, Salt Free | Salt Free, Sugar Free |
| Prime Rib Seasoning | Dry Rub, American, Steak Seasoning, Sugar Free |
| Pumpkin Pie Spice | Baking, Sugar Free |
| Puya Chiles, Dried | Chiles & Hot Peppers |
| Quatre epices | Pork Rubs, Mediterranean, Sugar Free |
| Ranch Dressing Seasoning | American |
| Ras El Hanout | Curry, Sugar Free |
| Recado Rojo Rub | Chicken Rubs, Mexican, Salt Free |
| Red Beans and Rice Seasoning | Cajun & Creole, Salt Free |
| Red Pepper Flakes | Chiles & Hot Peppers, Chile Flakes |
| Roasted Garlic Pepper | Pepper Blend, Salt Free, Sugar Free |
| Roasted Minced Onion | Onion |
| Rose Petals | Exotic |
| Ground Rosemary | Herbs |
| Rosemary Leaf | Herbs |
| Saffron | Spanish, Earthy, Exotic |
| Sage Leaf C/S | Herbs |
| Sage, Rubbed | Herbs |
| Saigon Cinnamon Sticks 2.75" | Cinnamon |
| Salt Free Cajun Seasoning | Cajun & Creole, Salt Free |
| Salt Free Poultry Seasoning | Salt Free |
| Salt Free Steak Rub | Dry Rub, Salt Free, Steak Seasoning |
| Salt, Celery | Salt |
| Salt, Garlic | Salt, Garlic |
| Salt, Hawaiian Alaea Red | Gourmet Salt |
| Salt, Sea | Salt |
| Savory | Herbs |
| Scotch Bonnet Chile Flakes | Chiles & Hot Peppers, Chile Flakes |
| Sea Salt | Salt |
| Seafood Boil | Seafood, American |
| Serrano Chiles | Chiles & Hot Peppers |
| Serrano, Ground | Chiles & Hot Peppers |
| Sesame Seed | Nutty |
| Sesame Seeds, Black | Nutty |
| Shawarma Seasoning | Middle Eastern, Salt Free, Chicken Rubs, Sugar Free |
| Shichimi Togarashi | Asian, Salt Free, Sugar Free |
| Sichuan Peppercorns | Asian, Peppercorns |
| Sicilian Bread Dipping Seasoning | Mediterranean, Bread Dipping Seasoning, Sugar Free |
| Sicilian Sea Salt | Gourmet Salt |
| Smoked Bourbon Barrel Salt | Gourmet Salt, Smoked Salt |
| Smoked Cherry Wood Salt | Gourmet Salt, Smoked Salt |
| Smoked Mesquite Sea Salt | Gourmet Salt, Smoked Salt |
| Smoked Paprika (Hot) | Paprika |
| Smoked Paprika (Sweet) | Paprika |
| Smoked Tea Rub | Pork Rubs |
| Smoky Citrus Salt | Gourmet Salt, Sugar Free |
| Smoked Hickory Salt | Gourmet Salt, Smoked Salt |
| Southwest Seasoning | American, Salt Free, Steak Seasoning, Sugar Free |
| Spaghetti Seasoning | American, Sugar Free |
| Spanish Saffron | Spanish |
| Spearmint Leaves, Dried | Herbs |
| Spicy Thai Seasoning | Asian, Salt Free, Sugar Free |
| St Louis Rib Rub | Dry Rub |
| Star Anise, Whole | Pickling Spice, Asian |
| Star Anise, Ground | Pickling Spice, Asian |
| Steak Rub | Dry Rub, Steak Seasoning |
| Steak Rub, Salt Free | Dry Rub, Salt Free |
| Sumac | Middle Eastern, Exotic |
| Summer Savory | Herbs |
| Sweet Basil | Herbs |
| Sweet Chili Powder | Chili Powder, Salt Free |
| Sweet Curry | Curry, Sugar Free |
| Sweet Italian Sausage Seasoning | Sausage |
| Taco Seasoning | Mexican, Salt Free |
| Tandoori Spice | Indian, Sugar Free |
| Tarragon Leaf | Herbs |
| Tellicherry Black Peppercorns | Peppercorns |
| Tempero Baiano | South American, Sugar Free |
| Texas Chicken Rub | Dry Rub, Chicken Rubs, Sugar Free |
| Texas Smoked Turkey Rub | Turkey, Chicken Rubs |
| Thai Chiles | Chiles & Hot Peppers |
| Thai Seasoning, Spicy | Asian, Salt Free |
| Thyme Leaf | Herbs |
| Thyme, Ground | Herbs |
| Tien Tsin Chiles | Chiles & Hot Peppers |
| Tikka Masala | Indian, Salt Free, Chicken Rubs, Sugar Free |
| Toasted Granulated Onion | Mexican |
| Tomato Flakes | American |
| Tomato Powder | Vegetable |
| Trinidad Curry | Caribbean, Sugar Free |
| Tropical Caribbean Turkey Rub | Turkey, Caribbean |
| Turkey Brine Seasoning | Turkey |
| Turkish Kofte Seasoning | Middle Eastern, Chicken Rubs, Sugar Free |
| Turmeric Powder | Earthy |
| Tunisian Five Spice | African Spice Blend, Salt Free, Sugar Free |
| Tuscany Bread Dipping Seasoning | Italian Spice Blend, Bread Dipping Seasoning, Sugar Free |
| Urfa Biber | Mediterranean, Chilies |
| Vadouvan Curry | Curry, Mediterranean, Salt Free, Sugar Free |
| Vanilla Beans, Bourbon | Vanilla |

TABLE 3-continued

| Name | Category |
| --- | --- |
| Vanilla Extract | Baking, Vanilla |
| Vegetable Soup Mix | Soup Blends, Sugar Free |
| Vermont Maple Sugar | Sugar |
| Vietnamese Cinnamon Powder | Cinnamon |
| Vietnamese Pork Rub | Pork Rubs |
| Vindaloo Curry | Curry, Salt Free, Sugar Free |
| White Pepper, Fine Grind | Pepper |
| White Peppercorns | Peppercorns |
| Wild for Salmon | Seafood, Salmon |
| Yellow Mustard Seed | Mustard |
| Yellow Mustard Seed Powder | Mustard |
| Za'atar (Israeli) | Middle Eastern, Sugar Free |
| Za'atar (Syrian) | Middle Eastern, Sugar Free |

The composition according to the present invention can be appropriately prepared by mixing the above-mentioned beetroot, salt, and additional food material, etc. The form of preparation is not limited, and can be selected from any forms of powder composition, liquid composition, paste composition, gel composition, etc. Preferred form is powder composition. The form of powder composition is more convenient because it is easy to mix with a food material and additional seasoning to be applied. Herein, the term "powder composition" is intended to mean a composition in a powder form, as a whole, including materials or a mixture thereof in a form of any of powder, granules, crystalline particles, and the like. For the preparation of such form of powder composition, it is convenient to form powder, granules, or crystalline particles of the above-mentioned beetroot, salt, additional food material, etc., in advance and appropriately mix them together. Another technique is dissolving each component in water, mixing the aqueous solutions together, and removing the water by vacuum to obtain the desired product. These techniques and other mixing techniques known to those skilled in the art can be used to obtain the salty taste composition according to the present invention as a desired product. For example, a freeze-dry method, spray-dry method, and the like can be suitably used for the preparation of the form of powder. The agitation granulation method, fluidized bed granulation method, extrusion granulation method, etc., can be suitably used for the preparation of the form of granules. Crystalline particles can be formed by slow cooling of a saturated solution.

In one embodiment of the present invention, the salty taste composition according to the present invention may contain dry solids in the form of salt, with or without dry solids of any other seasoning known to those skilled in the art. The salty taste composition may also contain other dry solids known to those skilled in the art including anti-caking agents, preservative agents, coating agents, coloring agents, diluents, bulking agents, and excipients for use in a production of products such as powder for oral administration and crystal-like products etc.

The compositions according to the present invention may be used to season a broad range of food, for example, as a substitute for a seasoning for food or cooking salt. In this case, the composition according to the present invention may be used in any processed food or non-processed food with adding to the food before, during, or after preparation for consumption of it at about 20 to 200%, preferably at about 50 to 175%, more preferably at about 75 to 150%, by mass of an ordinary salt content that would otherwise be used to achieve a comparable level of seasoning.

Examples of food to which the present invention is applied include a broad range of food products including soy sauce (shoyu), sauces, soups, breads, cookies, cakes, pies, frozen or refrigerated foods, baked foods, crackers, potato chips, canned vegetables, meats, and condiments.

Other examples of food to which the present invention is applied include what we call seasoning products, including dark-colored soy sauce (koikuchi shoyu), light-colored soy sauce (usukuchi shoyu), low-sodium soy sauce (gen-en shoyu), vinegar (su), miso, ryorishu (cooking sake), mirin, ponzu, shirodashi, mentsuyu, dashi, usuta sauce (worcester sauce), chuunou sauce, tonkatsu sauce, okonomi sauce, teriyaki sauce, oroshi sauce, mayonnaise (kewpie mayonnaise), wafu dressing, rayu (chili oil), goma abura (sesame oil), yuzukosho, wasabi, karashi, sansho, ichimi tougarashi, shichimi tougarashi, wagiri tougarashi, sesame, gomashio, aonori, katsuobushi, kezuribushi, furikake, seasoning with sodium glutamate, shouga (ginger), benishouga, shiso, yuzu, myoga, and daikon oroshi (grated radish).

As shown in Examples described later, the composition according to the present invention is palatable with enhanced salty taste and provides good salty taste, without deterioration of salty taste in spite of the reduced amount of salt, by virtue of the combination of beetroot and salt, where the salt masks the earthy taste of beetroot, and on the other hand, the beetroot enhances the salty taste of salt. Hence, the beetroot and salt in combination have an effect to reinforce mutually, and thus can be suitably used for the purpose of imparting a necessary and sufficient salty taste to a food with less salt than usual, by preparing a food so as to inherently contain them or adding them externally to a food. In this sense, the present invention provides a salty taste-imparting agent comprising beetroot and salt as active ingredients. Also, the present invention provides a method for seasoning a food with reduced salt by substituting a part of the salt in a salt-containing food with beetroot. Additionally, the present invention provides a method for producing a salt substitute containing salt and beetroot in combination.

As shown in Examples described later, the composition according to the present invention provides salty taste, and even if the salt content is reduced, the salty taste is comparable to that when the salt content is not reduced, through enhancement of the salty taste by beetroot. Hence, the beetroot mixed with salt has an effect to act as a salty taste enhancer, and thus can be suitably used for the purpose of imparting a salty taste to food by adding the composition of salt and beetroot inherently to the food during food preparation or by adding the composition externally to the food. In this sense, the present invention provides a salty taste enhancer comprising beetroot as the active ingredient. Also, the present invention provides a method for enhancing the salty taste of a food by adding beetroot to a salt-containing food, provided that the beetroot is effectively mixed with the salt in the food. For example, addition of beetroot to soy sauce wherein the beetroot is effectively mixed with the salt in the soy sauce can enhance the salty taste of the soy sauce. Additionally, the present invention provides a method for producing a salty taste enhancer comprising an effective amount of beetroot for enhancing salty taste.

As shown in Examples described later, the composition according to the present invention provides a superior effect to prevent an increase in blood pressure. Hence, it can be suitably used for a human with rather high blood pressure, that is, for administering to a human with hypertension, for administering to a human with prehypertension, for administrating to a human with normal blood pressure but who is concerned about their blood pressure, etc.

Herein, the term "hypertension" has a meaning as traditionally defined in the art, and specifically refers to a condition representing as a systolic blood pressure (SBP) equal to or greater than 140 mmHg and/or a diastolic blood pressure (DBP) equal to or greater than 90 mmHg. The term "prehypertension" herein has a meaning as traditionally defined in the art, and specifically refers to a condition representing as a SBP of equal to or greater than 120 and lower than 140 mmHg and/or a DBP of equal to or greater than 80 and lower than 90 mmHg. Further, the term "normal blood pressure" herein is defined as blood pressure not belonging to hypertension or prehypertension, such as a SBP under 120 mmHg and a DBP under 80 mmHg.

When being consumed by a human with hypertension or prehypertension, the composition according to the present invention can improve, treat, maintain/not to become worse than the present, or prevent an increase in blood pressure, or symptoms themselves that are related to the increased blood pressure associated with the hypertension or prehypertension, and reduce a risk of development of cardiovascular diseases and metabolic disorders caused by increased blood pressure and/or inflammation. Or when being consumed by a human with normal blood pressure, the composition according to the present invention can maintain the normal blood pressure not to become worse than the present, or prevent the normal blood pressure from worsening, and reduce the risk of development of cardiovascular diseases and metabolic disorders caused by increased blood pressure and/or inflammation.

Table 4 below shows medical disorders that involve salt-induced disturbances in nitric oxide activity and vascular function. Owing to their beneficial effects to reduce salt intake and improve nitric oxide activity, the compositions of the present invention can be particularly and suitably used to reduce health risk for the disorders in Table 4.

Because use of the salty taste compositions of the current invention in place of regular salt will reduce salt intake and simultaneously improve nitric oxide activity, they will also reduce a risk for clinical disorders mediated by disturbances in various inflammatory and immune system pathways that may be induced by excess salt intake and or subnormal nitric oxide activity, including salt-induced disturbances in interleukin pathways involving cytokines such as IL-6, IL-23, IL-10, IL-17 or others and the like. Without intending to restrict the scope of the current invention, the salty taste compositions of the current invention can thus be used to reduce a risk for the following clinical disorders in Table 5 below including common autoimmune disorders, inflammatory disorders, and neoplastic disorders known to be mediated or influenced by alterations in inflammatory pathways and or immune system function.

TABLE 5

| Multiple sclerosis | Psoriasis | Inflammatory Bowel disease | Crohn's disease | Osteoarthritis |
| Eczema | Sjogren's Syndrome | Neoplastic diseases | Asthma | Rheumatoid Arthritis |
| Ulcerative colitis | | | | |

Specific examples of neoplastic disorders in this Table 5 include but are not limited to: colon carcinoma, basal cell carcinoma, melanoma, squamous cell carcinoma, breast carcinoma, adenocarcinoma, sebaceous gland carcinoma, thyroid carcinomas, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryo-

TABLE 4

| Hypertension | Prehypertension | Salt-sensitivity | Salt-sensitive hypertension | Salt-resistant hypertension |
|---|---|---|---|---|
| Atherosclerosis | Myocardial infarction | Stroke | Transient ischemic attack | Mini-stroke |
| Peripheral vascular disease | Nephropathy | Diabetic nephropathy | Renal failure | Chronic renal failure |
| Microalbuminuria | Diabetes | Prediabetes | Metabolic syndrome | Insulin resistance |
| Type 1 Diabetes | Type 2 Diabetes | Obesity | Vascular dementia | Alzheimer disease |
| Erectile dysfunction | Congestive heart failure | Memory and cognitive dysfunction | IL-17 related immune disorders | |

It is now well established that alterations in body and tissue salt content can have significant effects on inflammatory pathways and immune cell function which can influence risk for a variety of clinical disorders that are modulated by the immune system (Kleinewietfeld M et al. Sodium Chloride Drives Autoimmune Disease by the Induction of Pathogenic Th17 Cells. Nature 2013 Apr. 25; 496(7446): 518-522; Amar S et al. Inflammatory role of high salt level in tumor microenvironment. International Journal of Oncology 50: 1477-1481, 2017; Zhou X, et al, Variation in dietary salt intake induces coordinated dynamics of monocyte subsets and monocyte-platelet aggregates in humans: implications in end organ inflammation. PLoS One. 2013 Apr. 4; 8(4): e60332; Schatz V, et al. Elementary immunology: Na+ as a regulator of immunity. Pediatr Nephrol (2017) 32:201-210; Zostawa J et al. The influence of sodium on pathophysiology of multiple sclerosis. Neurol Sci. 2017 March; 38(3):389-398; Hucke S et al. Implications of dietary salt intake for multiple sclerosis pathogenesis. Multiple Sclerosis Journal 2016, Vol. 22(2) 133-139).

nal carcinoma, lymphomas, cervical cancer, testicular tumor, lung carcinoma, small cell lung carcinoma, bladder carcinoma, and the like.

The form of use of the composition according to the present invention is not limited unless the effect is impaired. For example, the composition according to the present invention can be used in the form of a product such as a health food, functional food, nutritional supplementary food, supplement, animal health food, animal functional food, animal supplementary food, animal supplement, etc., or can be used with any of the products in combination. For example, the composition can also be prepared with a supplement such as a vitamin supplement in amounts known to those skilled in the art of preparing safe amounts of vitamin supplements for daily use. Examples of a preferred vitamin supplement are vitamin D in the form of 25OH vitamin D (also called as calcifediol, or 25-hydroxycholecalciferol) or 1,25-dihydroxy vitamin D3 (also called as calcitriol, or 1,25-dihydroxycholecalciferol), and/or vitamin C which is also called as L-ascorbic acid. Recently, it has been found that biologically active forms of vitamin D can stimulate nitric oxide release and there is evidence indicating that beneficial cardiovascular effects of vitamin D are mediated in part through increases in nitric oxide in the vasculature (Khan A, et al. Nanomedical studies of the restoration of nitric oxide/peroxynitrite balance in dysfunctional endothelium by 1,25-dihydroxy vitamin D3—clinical implications for cardiovascular diseases. International Journal of Nanomedicine 2018:13 455-466). In some embodiments, the compositions of the current invention would include the combination of beetroot and salt in the amounts described herein together with vitamin D wherein the composition contains approximately 5 to 40 International Units of 25OH vitamin D for every gram of salt in the composition or for every gram of the salty taste composition. A preferred amount of vitamin D in the composition would be 10 to 20 International Units of 25 OH vitamin D for every gram of salt in the composition or for every gram of the salty taste composition. The vitamin D in the composition would have the added benefit of improving nitric oxide activity, immune system function, and helping to maintain normal calcium metabolism and reduce the risks for urinary calcium loss and osteoporosis that are known to be associated with a high salt intake. In some embodiments, the compositions of the current invention would include the combination of beetroot and salt in the amounts described herein together with vitamin C (ascorbic acid) wherein the composition contains approximately 2 to 50 milligrams of vitamin C for every gram of salt in the composition or for every gram of the salty taste composition. A preferred amount of vitamin C in the composition would be 5 to 20 milligrams of vitamin C for every gram of salt in the composition or for every gram of the salty taste composition. The vitamin C in the composition would have the added benefit of decreasing oxidative stress and improving nitric oxide activity and immune system function. Here, the term "functional food" has a meaning including "food with functional characteristics" (FFC), "food for specialized health uses" (FOSHU), and "food with nutrient functional claims" (FNFC) according to the definitions used by the Japanese government.

EXAMPLES

Hereinafter, the present invention will be explained more specifically with Examples. The following Examples are presented to provide those skilled in the art with a more complete disclosure and description on how to implement and use the present invention. More specifically, Examples will demonstrate the ratios of beetroot and salt that can be used in preparation of a salty taste composition having a good salty taste and being capable of providing an amount of beetroot known to be sufficient to reduce the incidence of increased blood pressure while masking the earthy or other bad taste of beetroot. However, these Examples are neither intended to limit the scope of what the inventor regards as the invention, nor intended to represent all of the conceivable Examples. Any other form of beetroot can replace red beetroot or white beetroot, which are used in Examples.

Example 1

(Evaluation of Saltiness and Salty Taste of Various Salty Taste Compositions)

A series of salty taste compositions were prepared by blending different quantities of ordinary red beetroot powder ("red beet", produced by Asagiri firm, Kumamoto, JAPAN) with salt (produced by Morton Salt) as shown in Table 6. Five subjects were provided with the compositions for tasting, and then scored the sample compositions in terms of salty taste in accordance with the following graded evaluation shown below. For each test subject, the taste test was calibrated by first presenting a small sample on the tongue of approximately 10 mg of salt alone. The subject was informed that the sample was salt alone and was instructed to give a score of 3 to any other samples that have the same salty taste and flavor as this sample of salt alone. After this tasting, the subject was instructed to rinse out their mouth with water two times using distilled water provided in an 8 ounce glass. The subject was instructed that they would then be given mixtures of salt and a vegetable powder to taste and asked to report whether the sample tasted like salt alone or whether the sample tasted different from salt. Approximately 10 mg of the mixture was placed on the tongue and the subject instructed to move their tongue around to enable tasting in the whole mouth. If the sample tasted different from salt, the subjects were instructed to report a score of 2 for those samples with a bad taste flavor, or to report a score of 1 for those samples with a very bad taste flavor. The subjects were instructed to report a score of 4 for those samples that tasted salty and had a good taste flavor, or to report a score of 5 for those samples that tasted salty and had a very good taste flavor. For samples that were indistinguishable from salt with respect to salty taste and flavor, the subjects were instructed to report a score of 3. The identity of the salt compositions tested was coded so that neither the subject nor the test administrator was aware of the salt concentrations in the samples. After each tasting, the salt taste score was recorded on the sample list and the subject instructed to rinse out their mouth with water as before. The testing was then repeated for the next sample until all the samples were tested.

(Graded Evaluation)
Very bad taste: 1 point
Bad taste: 2 points
Indistinguishable from salt: 3 points
Salty and good taste: 4 points
Salty and very good taste: 5 points The results are shown in Table 6.

TABLE 6

| Beetroot (g) | Salt (g) | Salty Taste composition (g) | Ratio of beetroot/salt | Subject #1 | Subject #2 | Subject #3 | Subject #4 | Subject #5 |
|---|---|---|---|---|---|---|---|---|
| 0.1 | 10 | 10.1 | 0.01:1 | 3 | 3 | 3 | 3 | 3 |
| 0.2 | 10 | 10.2 | 0.02:1 | 3 | 3 | 3 | 3 | 3 |
| 0.3 | 10 | 10.3 | 0.03:1 | 3 | 3 | 3 | 3 | 3 |
| 0.5 | 10 | 10.5 | 0.05:1 | 3 | 3 | 4 | 3 | 3 |
| 1 | 10 | 11 | 0.1:1 | 3 | 3 | 4 | 3 | 3 |
| 2 | 10 | 12 | 0.2:1 | 3 | 3 | 4 | 3 | 4 |

TABLE 6-continued

| Beetroot (g) | Salt (g) | Salty Taste composition (g) | Ratio of beetroot/salt | Subject #1 | Subject #2 | Subject #3 | Subject #4 | Subject #5 |
|---|---|---|---|---|---|---|---|---|
| 5 | 10 | 15 | 0.5:1 | 4 | 4 | 5 | 3 | 5 |
| 8 | 10 | 18 | 0.8:1 | 5 | 4 | 5 | 5 | 5 |
| 10 | 10 | 20 | 1.0:1 | 5 | 4 | 5 | 5 | 5 |
| 12 | 10 | 22 | 1.2:1 | 5 | 4 | 5 | 5 | 5 |
| 15 | 10 | 25 | 1.5:1 | 4 | 4 | 5 | 5 | 5 |
| 18 | 10 | 28 | 1.8:1 | 4 | 5 | 4 | 3 | 3 |
| 20 | 10 | 30 | 2.0:1 | 1 | 4 | 1 | 2 | 2 |

The results of Table 6 revealed that a salty taste composition containing beetroot and salt in combination with a ratio of beetroot to salt by dry weight between 0.05:1 and 1.8:1 can provide an effectively salty and good taste. In contrast, it was found that the salty taste of a salty taste composition is difficult to distinguish from that of salt when the quantity of red beetroot powder blended is small, and a salty taste composition tastes the distinctive earthy taste of red beetroot and the bad taste is significant when the quantity of red beetroot powder is blended in ratios to salt that are above 1.8:1 (excessively large).

Example 2

(Evaluation of Various Amounts of Beetroot and Other Powders with Respect to the Salty Taste of Salty Compositions)

The study was conducted using a staircase test protocol in which stimulus sampling to assess the salty taste of different mixtures of sodium chloride dissolved in distilled water was carried out using a modified version of the "whole mouth sip and spit procedure" described by Wise and Breslin (2013). Details of the experimental procedure are described below. During each study, taste testers were given a series of solutions to test comprised of 5 mL samples presented in teaspoons. Each sample solution contained a specified amount of sodium chloride (produced by Morton Salt) with or without a specified amount of beetroot powder ("red beet", produced by Asagiri firm, Kumamoto, JAPAN), lactose powder (100% pure lactose obtained from the Now Foods company, Bloomingdale, Ill., USA), or cornstarch powder (100% pure cornstarch (brand name "Argo") obtained from ACH Food Companies, Inc, Memphis, Tenn., USA) dissolved in room temperature distilled water. The subject was instructed to take and hold the sample in their mouth for 5-10 seconds, spit out the sample, then rated the saltiness of the sample (wholemouth, sip-and-spit procedure as described by Wise and Breslin, 2013).

For each test subject, the lower limit of the salty taste scale of 0 was calibrated by first presenting a sample of distilled water alone. The subject was informed that the first sample contained no salt and was instructed to give a score of 0 (zero) to any other samples that completely lack the taste of salt. After this tasting, the subject was instructed to rinse out their mouth with water two times using distilled water provided in an 8 ounce glass. In each taste test subject, the upper limit of the salty taste scale of 100 was calibrated by presenting a sample of the salt water alone containing 0.4% sodium chloride in distilled water. This concentration range was greater than the minimum threshold for recognition of the salty taste of sodium chloride in >95% of test subjects as previously reported by Wise and Breslin (2013) and Giguère et al (2016). The subject was informed that the sample was salt water alone and was instructed to give a score of 100 to any other samples that have the same salty taste as this sample of salt alone. For samples perceived to be less salty than this pure sample of salt water alone, the subject was instructed to report a score of less than 100. After this tasting, the subject was instructed to rinse out their mouth with water two times using distilled water provided in an 8 ounce glass.

After tasting of the salt calibration samples was completed, the subject was presented with a series of test solutions with varying concentrations of salt and either beetroot, lactose, or cornstarch (see Table 7). The samples were presented in descending order of salt concentration and contained ascending orders of either beetroot, lactose, or cornstarch. The identity of the salt compositions on the list was coded so that neither the subject nor the test administrator was aware of the salt concentrations in the samples. The subject was asked to taste the sample using the whole mouth sip and spit procedure and to rate the samples for salty taste on the scale of 0 to 100 with 100 being the same saltiness as the salt water calibration sample and 0 being the saltiness of the sample of distilled water without salt. After this tasting, the salt taste score was recorded on the sample list and the subject instructed to rinse out their mouth with water as before. The testing was then repeated for the next sample until all the samples were tested. The mean taste test scores were then plotted against the salt concentrations of the various samples tested. The plotted results were then visually examined to look for differences between the beetroot, lactose, and cornstarch groups in the dose response curves for salty taste.

TABLE 7

| Ratio of test powder:sodium chloride by weight in the solution | | | Amount of test powder in mixture | Amount of NaCl in mixture |
|---|---|---|---|---|
| beetroot:NaCl | lactose:NaCl | Corn starch:NaCl | (% by weight) | (% by weight) |
| NaCl alone (no test powder) | NaCl alone (no test powder) | NaCl alone (no test powder) | 0% | 100% |
| ~1:16 | ~1:16 | ~1:16 | 6% | 94% |
| ~1:12 | ~1:12 | ~1:12 | 8% | 92% |

TABLE 7-continued

| Ratio of test powder:sodium chloride by weight in the solution | | | Amount of test powder in mixture | Amount of NaCl in mixture |
|---|---|---|---|---|
| beetroot:NaCl | lactose:NaCl | Corn starch:NaCl | (% by weight) | (% by weight) |
| ~1:7 | ~1:7 | ~1:7 | 12% | 88% |
| ~1:5 | ~1:5 | ~1:5 | 16% | 84% |
| ~1:4 | ~1:4 | ~1:4 | 20% | 80% |
| ~1:2 | ~1:2 | ~1:2 | 33.3% | 66.6% |

Experimental results showing how beetroot powder and other powders affect salty taste are shown in the FIG. 1.

Note that substituting lactose powder or cornstarch powder for sodium chloride caused a reduction in the salty taste of the sodium chloride when the percentage by weight of the lactose powder or cornstarch powder in the salt mixture exceeds 6% (when the ratio by weight of lactose or cornstarch to sodium chloride in the mixture exceeds ~1:16). In contrast, when beetroot powder was substituted for sodium chloride, the salty taste of sodium chloride was not affected until the percentage by weight of beetroot in the mixture exceeds 20% (not affected until the ratio by weight of beetroot powder to sodium chloride in the mixture exceeds ~1:4). Thus, ratios of beetroot powder:sodium chloride within the range of approximately 1:16 to 1:4 maintained a salty taste from the sodium chloride more effectively than the same ratios of lactose powder:sodium chloride or cornstarch powder:sodium chloride. Importantly, ingestion of compositions that contained ratios of beetroot powder:sodium chloride within this ~range of 1:16 to 1:4 provided amounts of nitrate in relation to sodium chloride (nitrate:sodium chloride ratios of ~1:160 to 1:40) that were sufficient to prevent the ingested sodium chloride from increasing blood pressure.

Example 3

(Salt Compositions that Contain Beetroot with Amounts of Nitrate Sufficient to Prevent Salt-Induced Increases in Blood Pressure)

The experiment was conducted in two groups of inbred Dahl salt sensitive rats, the most widely used animal model for testing the effects of salt intake on blood pressure. Radiotelemetry catheters were implanted in the abdominal aorta of each rat to provide continuous measurements of blood pressure 24 hours per day, seven days per week. At least 7-10 days after recovery from surgical implantation of the radiotransmitters, baseline blood pressure recordings were obtained while feeding all of the animals a low salt diet and tap water.

After approximately 7 days of BP recording on the low intake, salt intake was increased in one group of rats by replacing the drinking water with a salt water solution containing sodium chloride at a concentration of 10 grams per liter (1% NaCl). In the other group of rats, salt intake was increased by replacing the drinking water with a salt water solution containing sodium chloride at a concentration of 10.2 grams per liter (1.02% NaCl) together with an amount of beetroot sufficient to provide a nitrate concentration of approximately 63 milligrams per liter (a nitrate:sodium chloride ratio by weight of approximately 1:160). Given the amount of nitrate typically found in beet root, this is equivalent to a ratio of beetroot powder:salt of approximately 1:16.

Fluid intake was controlled to insure that the rats drinking the solution of sodium chloride plus beetroot consumed the same amount of fluid as the rats drinking the solution of sodium chloride alone. Thus, if anything, the rats drinking the solution of beetroot and salt (1.02% NaCl) consumed more salt than the rats drinking the solution of salt water alone (1% NaCl). Blood pressure recordings were continued to determine the effects on blood pressure of administering the high salt intake with beetroot to the blood pressure effects of administering the high salt intake without beetroot.
(Result)

The result is shown in FIG. 2. The daily intake of salt was controlled so that the group given beetroot with salt consumed at least as much salt as the group given salt alone. Thus, the lower blood pressure in the beetroot plus salt group is not due to lower salt intake in the beetroot plus salt group.

FIG. 2(*a*) shows 24-hour mean arterial pressures measured by radiotelemetry before and after initiating different treatments. FIG. 2(*b*) shows significantly lower blood pressures throughout treatment with beetroot and salt compared to treatment with salt alone (unpaired t test).

Example 4

(Effects of Red Beetroot and Shikuwasa/Application for Subjects with Normal Blood Pressure)

The compositions to provide in this examination are prepared as follows.
(1) Red Beetroot Powder Prepare 210 g of red beetroot powder, and then put it into 60 unit dose foil packages so that each package contains 3.5 g of red beetroot powder.
(2) Mixture of Red Beetroot Powder and Shikuwasa Powder A beetroot composition containing shikuwasa is prepared by thoroughly mixing 210 g of red beetroot powder with 30 g of shikuwasa powder, and then put into 60 unit dose foil packages so that each package contained 4 g of the mixture.
(3) Shikuwasa Powder 30 g of shikuwasa powder is prepared, and then put it into 60 unit dose foil packages so that each package contains 0.5 g of shikuwasa powder.

Eighteen adult subjects (9 men and 9 women) between the ages of 25 years and 60 years with normal blood pressure less than 120/80 mmHg are selected for testing the powder composition consisting of red beetroot powder alone in the above (1), the powder composition consisting of a mixture of red beetroot powder and shikuwasa powder in the above (2), and the powder composition consisting of shikuwasa powder alone in the above (3). Six of the subjects (3 men and 3 women) are assigned to a group to consume the powder composition consisting of red beetroot powder alone in the above (1), and six of the subjects (3 men and 3 women) are assigned to a group to consume the powder composition consisting of a mixture of red beetroot powder and shikuwasa powder in the above (2), and six of the subjects (3 men and 3 women) are assigned to a group to consume the powder composition consisting of shikuwasa powder alone in the above (3). Blood pressure measurement is performed for the subjects before the initiation of this examination, and the results are analyzed through a variance test to check for significant difference in blood pressure among the test groups.

Each of the subjects is instructed, once every day for 60 days, to mix one dose of the assigned composition with 120 mL of cold water and stir the mixture with a spoon for 15 to 30 seconds to prepare a liquid mixture, and to consume the liquid mixture. Each of the subjects is asked whether the liquid mixture consumed tasted earthy or tasted bad or dirty, and for each group the opinions from the subjects are summarized. After the 60-day consumption, blood pressure measurement is performed for the subjects.

Example 5

(Effects of Red Beetroot and Shikuwasa/Application for Subjects with Prehypertension)

The compositions to provide in this examination are prepared as follows.
(1) Red Beetroot Powder
Prepare 420 g of red beetroot powder, and then put it into 120 unit dose foil packages so that each package contains 3.5 g of red beetroot powder.
(2) Mixture of Red Beetroot Powder and Shikuwasa Powder
A beetroot composition containing shikuwasa is prepared by thoroughly mixing 420 g of red beetroot powder with 60 g of shikuwasa powder, and then put into 120 unit dose foil packages so that each package contains 4 g of the mixture.
(3) Shikuwasa Powder
Prepare 60 g of shikuwasa powder, and then put it into 120 unit dose foil packages so that each package contains 0.5 g of shikuwasa powder.

Eighteen adult subjects (ages of 55 years to 60 years, 9 men and 9 women) with prehypertension and systolic blood pressure of about 135 to 138 mmHg and diastolic blood pressure of about 85 to 88 mmHg are selected for testing the powder composition consisting of red beetroot powder alone in the above (1), the powder composition consisting of a mixture of red beetroot powder and shikuwasa powder in the above (2), and the powder composition consisting of shikuwasa powder alone in the above (3). Six of the subjects (3 men and 3 women) are assigned to a group to consume the powder composition consisting of red beetroot powder alone in the above (1), and six of the subjects (3 men and 3 women) are assigned to a group to consume the powder composition consisting of a mixture of red beetroot powder and shikuwasa powder in the above (2), and six of the subjects (3 men and 3 women) are assigned to a group to consume the powder composition consisting of shikuwasa powder alone in the above (3). Blood pressure measurement is performed for the subjects before the initiation of this examination, and the results are analyzed through a variance test to check for significant difference in blood pressure among the test groups.

Each of the subjects is instructed, once every day for 120 days, to mix one dose of the assigned composition with 120 mL of cold water and stir the mixture with a spoon for 15 to 30 seconds to prepare a liquid mixture, and to consume the liquid mixture. Each of the subjects is asked whether the liquid mixture consumed tasted earthy or tasted bad or dirty, and for each group the opinions from the subjects are summarized. After the 120-day consumption, blood pressure measurement is performed for the subjects.

Example 6

(Effects of Red Beetroot and Yuzu/Application for Subjects with Normal Blood Pressure)

The compositions to provide in this examination are prepared as follows.
(4) Red Beetroot Powder
Prepare 210 g of red beetroot powder, and then put it into 60 unit dose foil packages so that each package contains 3.5 g of red beetroot powder.
(5) Mixture of Red Beetroot Powder and Yuzu Powder
A beetroot composition containing yuzu is prepared by thoroughly mixing 210 g of red beetroot powder with 30 g of yuzu powder, and then put into 60 unit dose foil packages so that each package contains 4 g of the mixture.
(6) Yuzu Powder
Prepare 30 g of yuzu powder, and then put it into 60 unit dose foil packages so that each package contains 0.5 g of yuzu powder.

Eighteen adult subjects (9 men and 9 women) between the ages of 25 years and 60 years with normal blood pressure less than 120/80 mmHg are selected for testing the powder composition consisting of red beetroot powder alone in the above (4), and the powder composition consisting of a mixture of red beetroot powder and yuzu powder in the above (5). Six of the subjects (3 men and 3 women) are assigned to a group to consume the powder composition consisting of red beetroot powder alone in the above (4), and six of the subjects (3 men and 3 women) are assigned to a group to consume the powder composition consisting of a mixture of red beetroot powder and yuzu powder in the above (5), and six of the subjects (3 men and 3 women) are assigned to a group to consume the powder composition consisting of yuzu powder alone in the above (6). Blood pressure measurement is performed for the subjects before the initiation of this examination, and the results are analyzed through a variance test to check for significant difference in blood pressure among the test groups.

Each of the subjects is instructed, once every day for 60 days, to mix one dose of the assigned composition with 120 mL of cold water and stir the mixture with a spoon for 15 to 30 seconds to prepare a liquid mixture, and to consume the liquid mixture. Each of the subjects is asked whether the liquid mixture consumed tastes earthy or tastes bad or dirty, and for each group the opinions from the subjects are summarized. After the 60-day consumption, blood pressure measurement is performed on the subjects.

Example 7

(Effects of Red Beetroot and Yuzu/Application for Subjects with Prehypertension)

The compositions to provide in this examination were prepared as follows.
(4) Red Beetroot Powder
Prepare 420 g of red beetroot powder, and then put it into 120 unit dose foil packages so that each package contains 3.5 g of red beetroot powder.
(5) Mixture of Red Beetroot Powder and Yuzu Powder
A beetroot composition containing yuzu is prepared by thoroughly mixing 420 g of red beetroot powder with 60 g of yuzu powder, and then put into 120 unit dose foil packages so that each package contains 4 g of the mixture.
(6) Yuzu Powder Prepare 60 g of yuzu powder, and then put it into 120 unit dose foil packages so that each package contains 0.5 g of yuzu powder.

Eighteen adult subjects (ages of 55 years to 60 years, 9 men and 9 women) with prehypertension and systolic blood pressure of about 135 to 138 mmHg and diastolic blood pressure of about 85 to 88 mmHg are selected for testing the powder composition consisting of red beetroot powder alone in the above (4), the powder composition consisting of a mixture of red beetroot powder and yuzu powder in the above (5), and the powder composition consisting of yuzu powder alone in the above (6). Six of the subjects (3 men and 3 women) are assigned to a group to consume the powder composition consisting of red beetroot powder alone in the above (4), and six of the subjects (3 men and 3 women) are assigned to a group to consume the powder composition consisting of a mixture of red beetroot powder and yuzu powder in the above (5), and six of the subjects (3 men and 3 women) are assigned to a group to consume the powder composition consisting of yuzu powder alone in the above (6). Blood pressure measurement is performed for the subjects before the initiation of this examination, and the results are analyzed through a variance test to check for significant difference in blood pressure among the test groups.

Each of the subjects is instructed, once every day for 120 days, to mix one dose of the assigned composition with 120 mL of cold water and stir the mixture with a spoon for 15 to 30 seconds to prepare a liquid mixture, and to consume the liquid mixture. Each of the subjects is asked whether the liquid mixture consumed tastes earthy or tastes bad or dirty, and for each group the opinions from the subjects are summarized. After the 120-day consumption, blood pressure measurement is performed for the subjects.

Example 8

(Effects of Red Beetroot and Vegetables/Application for Subjects with Normal Blood Pressure)

The compositions to provide in this examination are prepared as follows.
(7) Red beetroot powder
(8) 1:1 mixture of red beetroot powder and komatsuna powder
(9) 1:1 mixture of red beetroot powder and ging-gen-cai powder
(10) 1:1 mixture of red beetroot powder and spinach powder
(11) 1:1 mixture of red beetroot powder and mitsuba powder Twenty adult subjects (10 men and 10 women) between the ages of 25 years and 60 years with normal blood pressure less than 120/80 mmHg are selected for testing the powder composition consisting of red beetroot powder alone in the above (7), the powder composition consisting of a mixture of red beetroot powder and komatsuna powder in the above (8), the powder composition consisting of a mixture of red beetroot powder and ging-gen-cai powder in the above (9), the powder composition consisting of a mixture of red beetroot powder and spinach powder in the above (10), and the powder composition consisting of a mixture of red beetroot powder and mitsuba powder in the above (11), and four of the subjects (2 men and 2 women) are assigned to a group to consume any of the powder compositions in the above (7) to (11). Blood pressure measurement is performed for the subjects before the initiation of this examination, and the results are analyzed through a variance test to check for significant difference in blood pressure among the test groups.

Each of the subjects is instructed, once every day for 60 days, to mix one dose, 5 g, of the assigned composition with 120 mL of cold water and stir the mixture with a spoon for 15 to 30 seconds to prepare a liquid mixture, and to consume the liquid mixture. Each of the subjects is asked to score the taste of the liquid composition consumed in accordance with the graded evaluation shown below, and the average score is determined for each group. After the 60-day consumption, blood pressure measurement is performed for the subjects.
(Graded Evaluation)
Very bad taste: 1 point
Bad taste: 2 points
Neutral taste: 3 points
Good taste: 4 points
Very good taste: 5 points Example 9

(Effects of Red Beetroot and Vegetables/Application for Subjects with Prehypertension)

The compositions to provide in this examination are prepared as follows.
(7) Red beetroot powder
(8) 1:1 mixture of red beetroot powder and komatsuna powder
(9) 1:1 mixture of red beetroot powder and ging-gen-cai powder
(10) 1:1 mixture of red beetroot powder and spinach powder
(11) 1:1 mixture of red beetroot powder and mitsuba powder Twenty adult subjects (ages of 55 years to 60 years, 10 men and 10 women) with prehypertension and systolic blood pressure of about 135 to 138 mmHg and diastolic blood pressure of about 85 to 88 mmHg are selected for testing the powder composition consisting of red beetroot powder alone in the above (7), the powder composition consisting of a mixture of red beetroot powder and komatsuna powder in the above (8), the powder composition consisting of a mixture of red beetroot powder and ging-gen-cai powder in the above (9), the powder composition consisting of a mixture of red beetroot powder and spinach powder in the above (10), and the powder composition consisting of a mixture of red beetroot powder and mitsuba powder in the above (11), and four of the subjects (2 men and 2 women) are were assigned to a group to consume any of the powder compositions in the above (7) to (11). Blood pressure measurement is performed for the subjects before the initiation of this examination, and the results are analyzed through a variance test to check for significant difference in blood pressure among the test groups.

Each of the subjects is instructed, once every day for 120 days, to mix one dose, 5 g, of the assigned composition with 120 mL of cold water and stir the mixture with a spoon for 15 to 30 seconds to prepare a liquid mixture, and to consume the liquid mixture. After the 120-day consumption, blood pressure measurement is performed for the subjects.

Example 10

Influence on Blood Pressure in Use of Salty Taste Composition Containing Beetroot and Salt as Salt Substitute Specifically, a salty taste composition is prepared as a 1:1 mixture by mass of salt and white beetroot powder, and the following test groups, the first group to the fourth group, are set-up to carry out a test for adult subjects.
(First Group)

Sixteen adult subjects (8 men and 8 women between the ages of 40 and 55 years) with prehypertension are instructed to use the salty taste composition in an amount similar to the amount of salt that they had used in the past (approximately 10 grams salt/day) for all of their cooking and food preparation in place of regular salt for a period of one year. The subjects are also instructed to avoid eating fast foods for a period of one year and to avoid eating in restaurants more than once per month. Before beginning use of the salty taste composition, the systolic and diastolic blood pressures of the subjects are measured and recorded according to methods known to those skilled in the art of measuring blood pressure. After 1 year of consuming the salty taste composition in place of regular salt, the blood pressures are similarly measured and recorded.

(Second Group)

Sixteen adult subjects (8 men and 8 women between the ages of 40 and 55 years) with prehypertension are instructed to use regular salt in an amount of about 5 grams salt/day for all of their cooking and food preparation for a period of one year. The other conditions are the same as those for the first group. The systolic and diastolic blood pressures of all the subjects are measured and recorded at the beginning and the end of the one-year period.

(Third Group)

Sixteen adult subjects (8 men and 8 women between the ages of 40 and 55 years) with prehypertension are instructed to use regular salt in an amount of about 10 grams salt/day for all of their cooking and food preparation for a period of one year. The other conditions are the same as those for the first group. The systolic and diastolic blood pressures of all the subjects are measured and recorded at the beginning and the end of the one-year period.

(Fourth Group)

Sixteen adult subjects (8 men and 8 women between the ages of 40 and 55 years) with prehypertension are instructed to use the salty taste composition in an amount twice as large as the amount of salt that they had used in the past (approximately 10 grams salt/day) for all of their cooking and food preparation in place of regular salt for a period of one year. The other conditions are the same as those for the first group. The systolic and diastolic blood pressures of all the subjects are measured and recorded at the beginning and the end of the one-year period.

The invention claimed is:

1. An enhanced food composition, comprising:
   a food having a salt content, wherein the food is selected from the group consisting of a sauce, a soup, and a condiment; and
   a nitrate-containing vegetable effectively mixed with the salt content of the food;
   wherein the ratio of nitrate-containing vegetable to salt content in the food is 1:16 to 1:4 based on the dry weight of the nitrate-containing vegetable and the salt content; and
   wherein the nitrate-containing vegetable is selected from the group consisting of beetroot, arugula, spinach, lettuce, radish, Chinese cabbage or combinations thereof.

2. The enhanced food composition of claim 1, wherein the ratio of nitrate-containing vegetable to salt content in the food is 1:16 to 1:8.

3. The enhanced food composition of claim 1, wherein the nitrate-containing vegetable is beetroot.

4. The enhanced food composition of claim 1, wherein the food having a salt content is a sauce and the sauce is a soy sauce.

5. The enhanced food composition of claim 1, wherein the nitrate-containing vegetable is in the form of a powder composition, a liquid composition, a paste composition, or a gel composition.

6. The enhanced food composition of claim 1, wherein the nitrate-containing vegetable is in the form of a powder composition.

7. The enhanced food composition of claim 1, further comprising a nitrate-containing food, a Vitamin D-containing food, a Vitamin C-containing food, or any combination thereof.

8. An enhanced food composition, comprising:
   a food having a salt content, wherein the food is selected from the group consisting of a sauce, a soup, and a condiment; and
   a nitrate-containing vegetable effectively mixed with the salt content of the food;
   wherein the amount of nitrate-containing vegetable present in the enhanced food composition is such that the nitrate to salt ratio in the enhanced food composition is 1:160 to 1:50 based on the dry weight of the nitrate and the salt; and
   wherein the nitrate-containing vegetable is selected from the group consisting of beetroot, arugula, spinach, lettuce, radish, Chinese cabbage or combinations thereof.

9. The enhanced food composition of claim 8, wherein the amount of nitrate-containing vegetable present in the enhanced food composition is such that the nitrate to salt ratio in the enhanced food composition is 1:160 to 1:80 based on the dry weight of the nitrate and the salt.

* * * * *